(12) United States Patent
Traish

(10) Patent No.: US 6,489,113 B1
(45) Date of Patent: Dec. 3, 2002

(54) IN-VITRO DIAGNOSTIC METHODS FOR DETERMINING WHETHER A PRIMARY BREAST TUMOR IS CLINICALLY METASTATIC

(75) Inventor: Abdulmaged M. Traish, Belmont, MA (US)

(73) Assignee: Boston University, Boston, MA (US)

( * ) Notice: Subject to any disclaimer, the term of this patent is extended or adjusted under 35 U.S.C. 154(b) by 0 days.

(21) Appl. No.: 09/685,836

(22) Filed: Oct. 7, 2000

Related U.S. Application Data

(63) Continuation of application No. 08/866,928, filed on May 30, 1997, now Pat. No. 6,159,702, which is a continuation-in-part of application No. 08/509,570, filed on Jul. 31, 1995, now Pat. No. 5,744,356.

(51) Int. Cl.[7] .......................... C12Q 1/68; G01N 33/48; C07N 21/04
(52) U.S. Cl. .............................. 435/6; 435/504; 436/64; 436/813; 436/815; 536/23.5
(58) Field of Search .......................... 436/64, 813, 815; 435/504, 6; 536/23.5

(56) References Cited

PUBLICATIONS

Traish et al, FASEB Journal, 1996, vol. 10, pp. A1144.*
Ma et al, Methods (Orlando), 1996, vol. 10, pp. 273–278, (abstract).*

* cited by examiner

*Primary Examiner*—Anthony C. Caputa
*Assistant Examiner*—Karen A. Canella
(74) *Attorney, Agent, or Firm*—David Prashker

(57) ABSTRACT

A system of diagnostic test methods are provided for diagnosing whether a primary breast tumor from an individual human subject is a clinically metastatic tumor. These in-vitro diagnostic methods detect and utilize the presence or absence of a 55 kilodalton protein for the DNA or the RNA coding for an expressing this protein as a marker and indicator of tumor metastasis. The test methods thus can detect either the presence of the protein itself, or its unique DNA, or its singular RNA individually or collectively. Each method of detection provides a reliable indicator and marker by which to clinically diagnose and determine if a primary tumor within the breast of a living human subject is now or will soon likely be a metastatic tumor.

2 Claims, 17 Drawing Sheets

ATG CAG AGT AAT AAA ACT TTT AAC TTG GAG AAG CAA AAC CAT ACT CCA AGA AAG CAT CAT

CAA CAT CAC CAC CAG CAG CAG CAC CAC CAG CAG CAA CAG CAG CAG CCG CCA CCA CCG CCA

ATA CCT GCA AAT GGG CAA CAG GCC AGC AGC CAA AAT GAA GGC TTG ACT ATT GAC CTG AAG

AAT TTT AGA AAA CCA GGA GAG AAG ACC TTC ACC CAA CGA AGC CGT CTT TTT GTG GGA AAT

CTT CCT CCC GAC ATC ACT GAG GAA GAA ATG AGG AAA CTA TTT GAG AAA TAT GGA AAG GCA

GGC GAA GTC TTC ATT CAT AAG GAT AAA GGA TTT GGC TTT ATC CGC TTG GAA ACC CGA ACC

CTA GCG GAG ATT GCC AAA GTG GAG CTG GAC AAT ATG CCA CTC CGT GGA AAG CAG CTG CGT

GTG CGC TTT GCC TGC CAT AGT GCA TCC CTT ACA GTT CGA AAC CTT CCT CAG TAT GTG TCC

AAC GAA CTG CTG GAA GAA GCC TTT TCT GTG TTT GGC CAG GTA GAG AGG GCT GTA GTC ATT

GTG GAT GAT CGA GGA AGG CCC TCA GGA AAA GGC ATT GTT GAG TTC TCA GGG AAG CCA GCT

GCT CGG AAA GCT CTG GAC AGA TGC AGT GAA GGC TCC TTC CTG CTA ACC ACA TTT CCT CGT

CCT GTG ACT GTG GAG CCC ATG GAC CAG TTA GAT GAT GAA GAG GGA CTT CCA GAG AAG CTG

GTT ATA AAA AAC CAG CAA TTT CAC AAG GAA CGA GAG CAG CCA CCC AGA TTT GCA CAG CCT

GGC TCC TTT GAG TAT GAA TAT GCC ATG CGC TGG AAG GCA CTC ATT GAG ATG CAG AAG CAG

CAG CAG GAC CAA GTG GAC CGC AAC ATC AAG GAG GCT CGT GAG AAG CTG GAG ATG GAG ATG

GAA GCT GCA CGC CAT GAG CAC CAG GTC ATG CTA ATG AGA CAG GAT TTG ATG AGG CGC AAG

GAA GAA CTT CGG AGG ATG GAA GAG CTG CAC AAC CAA GAG GTG CAA AAA CGA AAG CAA CTG

GAG CTC AGG CAG GAG GAA GAG CGC AGG CGC CGT GAA GAA GAG ATG CGG CGG CAG CAA GAA

GAA ATG ATG CGG CGA CAG CAG GAA GGA TTC AAG GGA ACC TTC CCT GAT GCG AGA GAG CAG

GAG ATT CGG ATG GGT CAG ATG GCT ATG GGA GGT GCT ATG GGC ATA AAC AAC AGA GGT GCC

ATG CCC CCT GCT CCT GTG CCA GCT GGT ACC CCA GCT CCT CCA GGA CCT GCC ACT ATG ATG

CCG GAT GGA ACT TTG GGA TTG ACC CCA CCA ACA ACT GAA CGC TTT GGT CAG CTG CTA ACA

ATG GAA GGA ATT GGG GCA ATT GGT GGA ACT CCT CCT GCA TTC AAC CGT GCA GCT CCT GGA

GCT GAA TTT GCC CCA AAC AAA CGT CGC CGA TAC TAA

```
86/1                                              116/11
ATG CAG AGT AAT AAA ACT TTT AAC TTG GAG AAG CAA AAC CAT ACT CCA AGA AAG CAT CAT
 M   Q   S   N   K   T   F   N   L   E   K   Q   N   H   T   P   R   K   H   H
146/21                                            176/31
CAA CAT CAC CAC CAG CAG CAG CAC CAC CAG CAG CAA CAG CAG CAG CCG CCA CCA CCG CCA
 Q   H   H   H   Q   Q   Q   H   H   Q   Q   Q   Q   Q   Q   P   P   P   P   P
206/41                                            236/51                    NMT4
ATA CCT GCA AAT GGG CAA CAG GCC AGC AGC CAA AAT GAA GGC TTG ACT ATT GAC CTG AAG
 I   P   A   N   G   Q   Q   A   S   S   Q   N   E   G   L   T   I   D   L   K
266/61                                            296/71
AAT TTT AGA AAA CCA GGA GAG AAG ACC TTC ACC CAA CGA AGC CGT CTT TTT GTG GGA AAT
 N   F   R   K   P   G   E   K   T   F   T   Q   R   S   R   L   F   V   G   N
326/81                                            356/91
CTT CCT CCC GAC ATC ACT GAG GAA GAA ATG AGG AAA CTA TTT GAG AAA TAT GGA AAG GCA
 L   P   P   D   I   T   E   E   E   M   R   K   L   F   E   K   Y   G   K   A
386/101                                           416/111
GGC GAA GTC TTC ATT CAT AAG GAT AAA GGA TTT GGC TTT ATC CGC TTG GAA ACC CGA ACC
 G   E   V   F   I   H   K   D   K   G   F   G   F   I   R   L   E   T   R   T
446/121                                           476/131
CTA GCG CAG ATT GCC AAA GTG GAG CTG GAC AAT ATG CCA CTC CGT GGA AAG CAG CTG CGT
 L   A   E   I   A   K   V   E   L   D   N   M   P   L   R   G   K   Q   L   R
506/141                                           536/151
GTG CGC TTT GCC TGC CAT AGT GCA TCC CTT ACA GTT CGA AAC CTT CCT CAG TAT GTG TCC
 V   R   F   A   C   H   S   A   S   L   T   V   R   N   L   P   Q   Y   V   S
566/161                                           596/171
AAC GAA CTG CTG GAA GAA GCC TTT TCT GTG TTT GGC CAG GTA GAG AGG GCT GTA GTC ATT
 N   E   L   L   E   E   A   F   S   V   F   G   Q   V   E   R   A   V   V   I
626/181                                           656/191
GTG GAT GAT CGA GGA AGG CCC TCA GGA AAA GGC ATT GTT GAG TTC TCA GGG AAG CCA GCT
 V   D   D   R   G   R   P   S   G   K   G   I   V   E   F   S   G   K   P   A
686/201                                           716/211
GCT CGG AAA GCT CTG GAC AGA TGC AGT GAA GGC TCC TTC CTG CTA ACC ACA TTT CCT CGT
 A   R   K   A   L   D   R   C   S   E   G   S   F   L   L   T   T   F   P   R
746/221                                           776/231
CCT GTG ACT GTG GAG CCC ATG GAC CAG TTA GAT GAT GAA GAG GGA CTT CCA GAG AAG CTG
 P   V   T   V   E   P   M   D   Q   L   D   D   E   E   G   L   P   E   K   L
806/241                                           836/251
GTT ATA AAA AAC CAG CAA TTT CAC AAG GAA CGA GAG CAG CCA CCC AGA TTT GCA CAG CCT
 V   I   K   N   Q   Q   F   H   K   E   R   E   Q   P   P   R   F   A   Q   P
866/261                                           896/271
GGC TCC TTT GAG TAT GAA TAT GCC ATG CGC TGG AAG GCA CTC ATT GAG ATG GAG AAG CAG
 G   S   F   E   Y   E   Y   A   M   R   W   K   A   L   I   E   M   E   K   Q
926/281                                           956/291
CAG CAG GAC CAA GTG GAC CGC AAC ATC AAG GAG GCT CGT GAG AAG CTG GAG ATG GAG ATG
 Q   Q   D   Q   V   D   R   N   I   K   E   A   R   E   K   L   E   M   E   M
986/301                                           1016/311
GAA GCT GCA CGC CAT GAG CAC CAG GTC ATG CTA ATG AGA CAG GAT TTG ATG AGG CGC CAA
 E   A   A   R   H   E   H   Q   V   M   L   M   R   Q   D   L   M   R   R   Q
1046/321                                          1076/331
GAA GAA CTT CGG AGG ATG GAA GAG CTG CAC AAC CAA GAG GTG CAA AAA CGA AAG CAA CTG
 E   E   L   R   R   M   E   E   L   H   N   Q   E   V   Q   K   R   K   Q   L
1106/341                                          1136/351
GAG CTC AGG CAG GAG GAA GAG CGC AGG CGC CGT GAA GAA GAG ATG CGG CGG CAG CAA GAA
 E   L   R   Q   E   E   E   R   R   R   R   E   E   M   R   R   Q   Q   E
1166/361                                          1196/371        NMT5
GAA ATG ATG CGG CGA CAG CAG GAA GGA TTC AAG GGA ACC TTC CCT GAT GCG AGA GAG CAG
 E   M   M   R   R   Q   Q   E   G   F   K   G   T   F   P   D   A   R   E   Q
1226/381                                          1256/391
GAG ATT CGG ATG GGT CAG ATG GCT ATG GGA GGT GCT ATG GGC ATA AAC AAC AGA GGT GCC
 E   I   R   M   G   Q   M   A   M   G   G   A   M   G   I   N   N   R   G   A
1286/401                                          1316/411
ATG CCC CCT GCT CCT GTG CCA GCT GGT ACC CCA GCT CCT CCA GGA CCT GCC ACT ATG ATG
 M   P   P   A   P   V   P   A   G   T   P   A   P   P   G   P   A   T   M   M
1346/421                                          1376/431
CCG GAT GGA ACT TTG GGA TTG ACC CCA CCA ACA ACT GAA CGC TTT GGT CAG GCT GCT ACA
 P   D   G   T   L   G   L   T   P   P   T   T   E   R   F   G   Q   A   A   T
1406/441                                          1436/451                 NMT1
ATG GAA GGA ATT GGG GCA ATT GGT GGA ACT CCT CCT GCA TTC AAC CGT GCA GCT CCT GGA
 M   E   G   I   G   A   I   G   G   T   P   P   A   F   N   R   A   A   P   G
1466/461                                          1496/471
GCT GAA TTT GCC CCA AAC AAA CGT CGC CGA TAC TAA
 A   E   F   A   P   N   K   R   R   R   Y   *
```

FIG. 12

RNA Binding Domain

| | | | | | |
|---|---|---|---|---|---|
| nmt55 | 75 RLFVGNLPPD | ITEEEMRKLF | EKYGKAGEVF | IHKDKGFGFI | RLETRTLAEI |
| HeLa p54nrb | 75 RLFVGNLPPD | ITEEEMRKLF | EKYGKAGEVF | IHKDKGFGFI | RLETRTLAEI |
| Mouse NonO | 77 RLFVGNLPPD | ITEEEMRKLF | EKYGKAGEVF | IHKDKGFGFI | RLETRTLAEI |
| PSF | 298 RLFVGNLPAD | ITEDEFKRLF | AKYGEPGEVE | INKGKGFGFI | KLESRALAEI |
| NonA/BJ6 | 303 RLYVGNLTND | ITDDELREMF | KPYGEISEIF | SNLDKNFTFL | KVDYHPNAEK |

| | | | | | |
|---|---|---|---|---|---|
| nmt55 | 125 AKVELDNMPL | RGKQLRVRFA | CHSASLTVRN | LPQYVSNELL | EEAFSVFGQV |
| HeLa p54nrb | 125 AKVELDNMPL | RGKQLRVRFA | CHSASLHVRN | LPQYVSNELL | EEAFSVFGQV |
| Mouse NonO | 127 VKVELDNMPL | RGKQLRVRFA | CHSASLTVRN | LPQYVSNELL | EEAFSVFGQV |
| PSF | 348 AKAELDDTPM | RGRQLRVRFA | THAAALSVRN | LSPYVSNELL | EEAFSQFGPI |
| NonA/BJ6 | 353 AKRALDGSMR | KGRQLRVRFA | PNATILRVSN | LTPFVSNELL | YKSFEIFGPI |

| | | | | | |
|---|---|---|---|---|---|
| nmt55 | 175 ERAVVIVDDR | GRPSGKGIVE | FSGKPAARKA | LDRCSEGSFL | LTTFPRPVTV |
| HeLa p54nrb | 175 ERAVVIVDDR | GRPSGKGIVE | FSGKPAARKA | LDRCSEGSEL | LTTFPRPVTV |
| Mouse NonO | 177 ERAVVIVDDR | GRPSGKGIVE | FSGKPAARKA | LDRCSEGSFL | LTTFPRPVTV |
| PSF | 398 ERAVVIVDDR | GRSTGKGIVE | FASKPAARKA | FERCSEGVFL | LTTTPRPVIV |
| NonA/BJ6 | 403 ERASITVDDR | GKHMGEGIVE | FAKKSSASAC | LRMCNEKCFF | LTASLRPCLV |

| | |
|---|---|
| nmt55 | 225 EPMD (SEQ ID NO: 5) |
| HeLa p54nrb | 225 EPMD (SEQ ID NO: 6) |
| Mouse NonO | 227 EPMD (SEQ ID NO: 7) |
| PSF | 448 EPLE (SEQ ID NO: 8) |
| NonA/BJ6 | 453 EPME (SEQ ID NO: 9) |

FIG. 13

Helix Turn Helix Motif

| | | |
|---|---|---|
| nmt55 | 287 | RNIKEAREKL EMEMEAARHE HQVMLMRQDL MRRQEELRRM EELHNQEVQ (SEQ ID NO:10) |
| HeLa p54nrb | 287 | RNIKEAREKL EMEMEAARHE HQVMLMRQDL MRRQEELRRM EELHNQEVQ (SEQ ID NO:11) |
| Mouse NonO | 289 | RNIKEAREKL EMEMEAARHE HQVMLMRQDL MRRQEELRRM EELHNQEVQ (SEQ ID NO:12) |

FIG. 14

IN-VITRO DIAGNOSTIC METHODS FOR DETERMINING WHETHER A PRIMARY BREAST TUMOR IS CLINICALLY METASTATIC

CROSS-REFERENCE

This is a continuation of application Ser. No. 08/866,928, filed on May 30, 1997, now U.S. Pat. No. 6,159,702, which is a Continuation-In-Part of U.S. patent application Ser. No. 08/509,570 filed Jul. 31, 1995, now U.S. Pat. No. 5,744,356.

FIELD OF THE INVENTION

The present invention is generally concerned with breast cancer predictors of clinical prognosis; and is particularly directed to a system of in-vitro test methods for diagnosing whether a primary breast tumor from an individual human subject is a clinically metastatic tumor.

BACKGROUND OF THE INVENTION

The magnitude of the breast cancer problem today emphasizes the recurring and continuing need to determine the best possible predictors of prognosis so that appropriate therapy can be selected on an individual basis for women suffering from this common and dreaded disease. In the United States, breast cancer is the most common malignant neoplasm occurring in women, accounting for about 28 percent of the total cases. There is a noted increase in the number of breast cancers over recent decades. For example, in 1965, it was projected that 1 out of every 17 women (about 6 percent) would develop breast cancer. However, in 1989, the projection for breast cancer development is 1 in women (about 10 percent). This is believed due chiefly to the fact that there 10 are more women and that women are living longer into the cancer-prone years. It will be historically noted that for almost 100 years, the nineteenth century "Halstedian" hypothesis on breast tumor biology was the basis for breast cancer therapy. This hypothesis was a mechanistic concept postulating that cancer spread in an orderly fashion, progressing in a centrifugal manner from the breast to the regional lymph nodes, and ultimately to more distant anatomical sites. It postulated that breast cancers were local at the time of onset; that regional nodes serves as a barrier to local spread; that removal of the involved regional nodes influenced the survival of the patient; and that the type of local-regional therapy employed affected the survival of the patient. Implicit in this hypothesis was the concept that cancer could be held up for a time in the lymph nodes and that adequate removal of the breast with en-block dissection to the regional lymph nodes could effect a "cure." This theory supported the use of the radical and extended radical mastectomies, sometimes with adjuvant radiotherapy, as the best means for obtaining local-regional control. The role of direct hematogenous spread was not considered important; and thus systemic dissemination was not included in the concept [Halsted, W. S., *Johns Hopkins Hosp. Rep.* 2: 227 (1890–1891)].

The "Halstedian" hypothesis was challenged by MacDonald in 1951 [*Surg. Gynecol. Obstet*. 92: 443 (1951); *Am. J. Surg*. 111: 435 (1966)]. MacDonald suggested that human breast cancer was biologically determined from its onset. He stated that he had failed to find any evidence that early diagnosis, size of the tumor, or type of surgery had an influence on the outcome in mammary carcinoma. This report was followed by a period of marked pessimism regarding this form of cancer.

In the late 1970s, an alternative hypothesis to the "Halstedian" concept, based on animal experiments and the failure of some clinical trials to demonstrate the superiority of en-block dissection was advanced by Fisher and his collaborators [Fisher et al., *Cancer* 46: 1009–1025 (1980)]. The Fisher hypothesis stressed the importance of hematogenous dissemination of the cancer; and postulated that breast cancers were systemic at the time of onset, that regional nodes were not effective as barriers to systemic spread but rather were only indicators of biological behavior and metastatic potential as determined by a complex tumor-host interaction. Moreover, he believed that the removal of involved nodes had little influence on patient survival; and the type of local-regional therapy did not substantially affect survival. His hypothesis suggests that the only impact that could be made on breast cancer was by effective systemic therapy. It supported the use of lesser surgical procedures, with or without radiation, the use of adjuvant systemic chemoendocrine therapy, and the performance of axillary node dissections for staging purposes only.

Present authorities believe that neither of these 20th century hypotheses can be accepted in its entirety. Both modern hypotheses have elements of truth and are involved in explaining clinical events. Thus, these hypotheses should not be considered as mutually exclusive. Some cancers are observed to be very aggressive, producing early disseminated metastases and require adjuvant systemic therapy in addition to the local-regional removal of the tumor. Other cancers are much less aggressive, rarely making a transition to metastatic disease; and can be treated adequately by local-regional therapy without systemic adjuvant therapy. A more complete and detailed review and discussion of these hypotheses and clinical features can be found in The Breast on Comprehensive Management Of Benign And Malignant Diseases (Bland and Copeland, editors), W. B. Saunders Company, 1991, the text of which is expressly incorporated by reference herein.

There are a number of predictive parameters employed clinically for determining the prognosis of patients with breast cancers. Such predictors of prognosis have a variety of different origins and are often used in different combinations to provide a better evaluation and result. One source of predictors is based on the anatomical extent of the cancer in the patient. The predictors thus include staging, tumor size, tumor margins, axillary node status, and tumor location within the breast. A second source of predictors is based on the tumor growth potential (aggressive or virulence). These predictors include invasive quality of the tumor, multicentricity, histological types, histological grading, growth rate (cell kinetics), the presence or absence of steroid hormone receptors such as estrogen and progesterone receptors, as well as specific biological markers such as carcinoembryonic antigen (CEA) measurements, ferritin, C-reactive protein, acid glycoprotein, alkaline phospatase, silayl transferance and urinary hydroxyproline-creatinine ratios.

More recently, the discovery of tumor-specific genes that lead to tumor metastasis has become important in the development of strategies for treatment of breast cancer patients. The existence of specific genes responsible for suppression of tumor metastasis has been reported [Ramshaw et al., *International Journal of Cancer* 32: 471, 478 (1983)]. Several genetic markers are now used in assessing tumor changes and are linked to poor prognosis for the patient. These include amplification of erbB2/HER2/neu gene [Santes et al., *Cancer Res*. 52: 1916–1920 (1992); and Slamon et al., *Science* 244: 707–712 (1989)]; and a measured decrease in activity of the nm23 gene [Barnes et al., *American Journal of Pathology* 139: 245–250 (1991)].

In addition, over the past several years, a number of proteins have been implicated in the aberrant growth of human breast cancer cells. These included: epidermal growth factor receptor [Slamon et al., *Science* 244: 707–712 (1989)]; p53 protein [Weinberg, R. A., *Science* 254: 1138–1146 (1991)] a transcriptional factor with tumor suppresser properties; and the nm23 protein, a putative metastatic suppresser [Barnes et al., *Am. J. Pathol.* 139: 245–250 (1991)].

Today, even better predictors of prognosis are constantly being sought. In 1980, the NIH re-emphasized the importance of reliable prognostic factors by establishing grants to stimulate studies that search for parameters based on histological, histochemical, immunochemical, or other methods that would permit a more precise prediction of prognosis for patients with breast cancers. The ultimate goal is to be able to select the individual patients who can be treated adequately by breast conservation procedures, without any systemic adjuvant therapy; and to define the best type of treatment, both local-regional and systemic, for all other patients so as to offer them the best possible results.

In this continuing search for reliable predictors, there is and remains an urgent need for identification of node-negative patients whose primary tumors have a metastatic potential. The presently known tumor markers, even including evaluation of estrogen and progesterone receptor proteins, do not provide sufficient accuracy and precision and do not offer means for predicting with completely reliability which node-negative breast cancer patients will be likely to have metastatic dissemination. The development of a reliable metastatic marker or indicator, especially in the context of an in-vitro test methodology, would be recognized as a major advance and achievement in this field.

SUMMARY OF THE INVENTION

The present invention has multiple aspects and is definable in the alternative as a system of diagnostic test procedures. A first aspect of the invention provides an in-vitro protein test method for diagnosing whether a primary breast tumor from an individual human subject is a clinically metastatic tumor, said in-vitro protein test method comprising the steps of:

obtaining a specimen of breast tumor cells representative of a primary tumor found clinically in the breast of an individual human subject;

fractionating said specimen to yield the proteinacous matter from the nuclear portion of the primary breast tumor cells as a discrete fraction;

separating at least a part of said proteinaceous matter fraction from said fractionated primary breast tumor cell specimen; and detecting an absence of the nmt55 protein in said separated proteinaceous matter fraction, said detected absence of the nmt55 protein in said proteinaceous matter indicating that the primary breast tumor found in the individual human subject is a clinically metastatic tumor.

A second aspect of the present invention provides an in-vitro RNA test method for diagnosing whether a primary breast tumor from an individual human subject is a clinically metastatic tumor, said in-vitro RNA test method comprising the steps of:

obtaining a specimen of breast tumor cells representative of a primary tumor found clinically in the breast of an individual human subject;

fractionating said specimen to yield the RNA from the cellular components of the primary breast tumor cells as a discrete fraction;

separating at least a part of said RNA fraction from said fractionated primary breast tumor cell specimen; and detecting an absence of RNA specifically coding for the nmt55 protein in said separated RNA fraction, said detected absence of RNA specifically coding for the nmt55 protein in said separated RNA indicating that the primary breast tumor found in the individual human subject is a clinically metastatic tumor.

A third aspect of the present invention provides an in-vitro DNA test method for diagnosing whether a primary breast tumor from an individual human subject is a clinically metastatic tumor, said in-vitro DNA test method comprising the steps of:

obtaining a specimen of breast tumor cells representative of a primary tumor found clinically in the breast of an individual human subject;

fractionating said specimen to yield unclear DNA from the nuclear components of the primary breast tumor cells as a discrete fraction;

separating at least a part of said nuclear DNA fraction from said fractionated primary breast tumor cell specimen; and detecting an absence of DNA specifically coding for the nmt55 protein in said separated DNA fraction, said detected absence of DNA specifically coding for the nmt55 protein in said separated DNA indicating that the primary breast tumor found in the individual human subject is a clinically metastasis tumor.

BRIEF DESCRIPTION OF THE FIGURES

The present invention may be more easily understood and better appreciated when taken in conjunction with the accompanying drawing, in which:

FIG. 1 is a recitation of the amino acid residue composition for the nmt55 kDa protein;

FIG. 2 is a recitation of the cDNA base sequence coding for the nmt55 kDa protein;

FIG. 9 is a photograph of a Southern blot analysis of nmt55 genomic DNA isolated from human placenta;

FIG. 12 is a recitation of the DNA base sequence coding and the corresponding amino acid residue sequencing for the nmt55 kDa protein;

FIG. 13 is a recitation of the RNA binding domain for the nmt55 kDa protein in comparison to other RNA bindings proteins;

FIG. 14 is a recitation of the helix turn/helix motif for the nmt55 protein in comparison to other ligands;

DETAILED DESCRIPTION OF THE INVENTION

Figure 3:
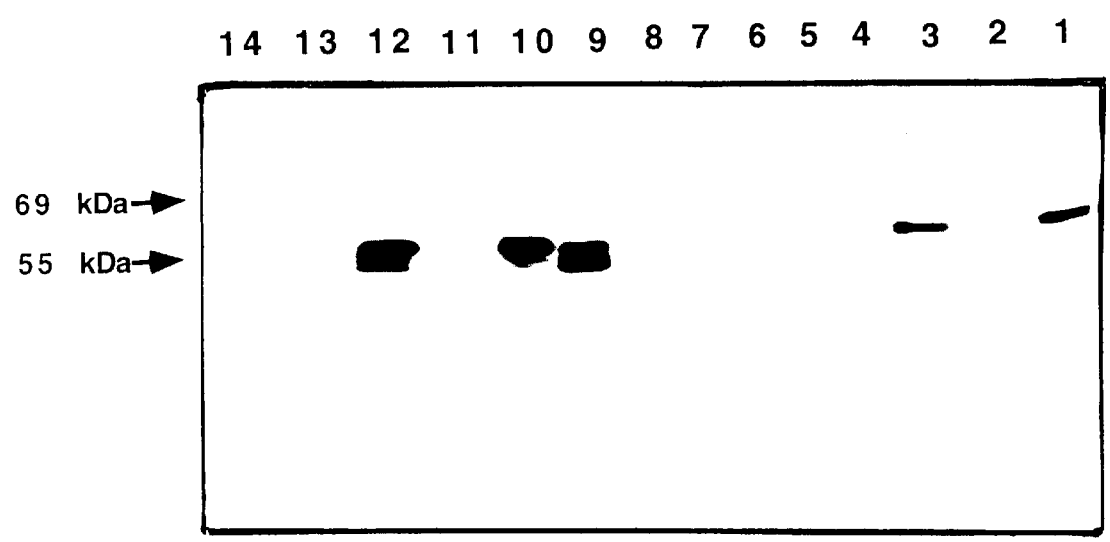
FIG. 3 is a photograph of a Western blot analysis showing the presence of the nmt55 kDa protein in human breast tumor nuclear extract using NMT-1 monoclonal antibody.

The present invention is a system of test procedures for diagnosing in-vitro whether a primary breast tumor specimen taken from or representative of the tumor in an individual human subject is now or is likely soon to be a clinically metastatic tumor. The entire system of test procedures relies on the existence of a nuclear 55 kilodalton protein and/or the genomic oligonucleotides (DNA and RNA) coding for and expressing this protein in primary tumor cells. Accordingly, the present invention has multiple benefits and major advantages which are not known or foreseen in this art. These include the following:

1. The in-vitro diagnostic methods comprising the present invention rely on a direct determination that the nmt55 protein is either present or absent in the primary tumor cells from the breast of the individual patient. The presence of the nmt55 protein or the DNA or RNA expressing this nmt55 protein is a direct and reliable marker that the tumor cells are not metastatic. In the alternative, if there is a detected absence of the nmt55 protein or the DNA or RNA coding for the protein, this absence identifies and signifies that the tumor in the living patient will now or will soon develop metastatic lesions. The diagnostic test procedures are thus simple absence or presence determinations, thereby reducing the likelihood of false positives, false negatives, and indeterminate test results.

2. The test methods of the present invention employ any clinical specimen as the test material so long as the specimen is a cellular tissue sample taken directly from or representative of a primary tumor in the breast of a living subject. The test diagnostic methodology is expected to be utilized primarily with malignant tumor samples and tumor specimens which are clinically difficult to evaluate using any other technique. In addition, the present methods can be employed as confirmatory procedures with recognized benign tumors and even normal tissue samples if such confirmation is desired or needed to establish that a particular tumor or tissue sample is not metastatic in nature.

3. The present invention utilizes a single system of methods, each of which is directed to one mode of detecting the presence or absence of the nmt55 protein, the RNA transcript, or the DNA gene in the cell sample. In the preferred and most reliable mode of analysis, the method detects the absence or presence of nmt55 protein directly from the nuclear components of the cells. In the alternative, however, either the DNA and/or the RNA may be detected as a specific sequence of oligonucleotide coding for and expressing the nmt55 protein within the cells. Any of these methods and protocols may be employed individually or in combination as a diagnostic technique in order to determine the absence or presence of nmt55 protein or genetic material within the test specimen.

4. The present invention can employ cellular specimens for evaluation without regard to whether these are fresh or frozen samples; without regard to whether these are biopsy specimens or surgical samples resulting from mastectomy; or, in extreme cases, when the sample is a pathological tissue sample obtained after autopsy. All that is required is that the cell specimen be relatively undamaged, be maintained or preserved in its original, intact state; and that the tissue sample remain unadulterated and uncontaminated up to the time of in-vitro testing.

It will be recognized and appreciated that the subject matter as a whole which is the present invention concerns itself with a very sophisticated and sometimes technically difficult medical problem; and that a general familiarity and understanding of cancer in general and breast tumors in particular is essential in order to properly understand the present invention. It is therefore important to employ some basic definitions and terms properly and precisely and to relate them to a clinical context. Many clinical and medical terms regarding breast cancer have a more precise meaning than is commonly appreciated. For this reason, a set of definitions and terminology is presented below which will be employed repeatedly in the description which follows hereinafter.

Definitions and Terminology:

Neoplasm: an abnormal mass of cells typically exhibiting uncontrolled and progressive growth. Neoplasms are broadly classified into two categories: (1) according to the cell type from which they originate; and (2) according to their biologic behavior, i.e., whether they are benign or malignant.

Breast tumors: neoplasms of the breast. Most breast tumors are epithelial in type. Breast carcinoma is the most common malignant neoplasm and currently accounts for 26 percent of all cancers in females within the U.S. The most frequently found benign breast tumor is the fibroadenoma.

Cancer: a general term that by common usage has come to encompass all forms of malignant neoplasms.

Malignant: a concept referring to the tendency to become progressively worse and to result in death. With neoplasms, the term denotes the properties of invasiveness and metastasis.

Benign: mild, favorable or kindly; in oncology, the opposite of malignant. Benign neoplasms are usually well circumscribed and are often encapsulated; by definition, benign tumors do not invade locally and do not metastasize.

Metastasis: the process by which malignant cells are disseminated from the tumor of origin (the primary tumor) to form a new growth (the secondary tumor) at a distant site. It is the discontinuous extension of a malignant neoplasm.

Tumor stage or staging: a general clinical guide that helps determine treatment and prognosis. A general TNM (T=tumor, N=nodes, M=metastasis) approach for assigning clinical stage uses the following scheme:

| Stage | | Prognosis |
|---|---|---|
| I. | T < 2 diameter, N = 0, M = 0 | best |
| II. | T < 5 cm, N+, M0; or T > 5 cm, N0, M0 | |

-continued

| Stage | | Prognosis |
|---|---|---|
| III. | Any T, N+, M0 | |
| IV. | Any T, N±, M+ | worst |

Tumor grade: a clinical method of predicting the biologic behavior of malignant neoplasms, and by extension, of prognosticating patient outcome from the assessment of certain cytologic and histologic features of the neoplasm. Typically, the evaluation uses a scale of three or four grades. Grade 1 represents tumors with the best differentiation; while the highest grade (3 or 4) represents tumors with the poorest differentiation. In general, the poorer the degree of differentiation, the higher the grade number, the more aggressive the tumor and the worse the prognosis.

Also, for easier comprehension and a better appreciation of the features and attributes for the present invention as a whole, the detailed disclosure will be presented in separate sections seriatim. The order of presentation will be: a description of the clinical specimens intended for evaluation; a disclosure and characterization of the nmt55 protein and the DNA expressing the protein in-vivo; evidence of clinical utility and diagnostic operability for the system of methods; a review of different assay procedures to detect the nmt55 protein in tumor cells; a review of different assays to detect DNA and RNA coding for and expressing nmt55 protein in tumor cells; illustrative preferred protocols for practicing the methods of the invention; and a description of experiments and presentation of empirical data demonstrating the major advantages and unusual properties provided by the present invention. Each of these will be described in detail below.

I. The Clinical Specimen: Primary Breast Tumors

The present diagnostic methodology is directed to the testing of a human breast tumor cell specimen in-vitro to determine whether or not the primary tumor found clinically within the patient is now metastatic or is soon likely to become metastatic. The entire broad class of human breast tumors is suitable for such diagnostic testing and includes malignant tumors such as the breast carcinomas and the relatively rare breast sarcomas. Breast carcinomas may arise from duct cells or from the terminal secretory units of breast lobules. More than 70 percent of reported cases are infiltrating duct cell carcinomas.

Breast tumors generally and breast carcinomas in particular are frequently diagnosed from a tissue biopsy or a needle aspiration specimen. When a mammogram fails to provide a firm diagnosis, excisional biopsy with specimen radiography prior to selection of areas for tissue section evaluation is often performed. Tissue is usually routinely submitted from a breast carcinoma for estrogen and progesterone receptor analyses as well.

Malignant breast carcinomas are typically categorized as being noninvasive or invasive. The noninvasive breast carcinomas include intraductal carcinoma in-situ (arising in the mammary ducts and not invading the surrounding stroma); and lobular carcinoma in-situ (involving the intralobular ductiles). In contrast, the recognized types of invasive breast carcinomas include (a) invasive duct cell carcinomas; (b) medullary carcinomas; (c) mucinous carcinomas; (d) tubular carcinomas; (e) inflammatory carcinomas; (f) invasive lobular carcinomas; and (g) Paget's disease. Each of these invasive types has its individual characteristics, histological definitions and features, and prognosis. The biological behavior of these invasive breast carcinomas today is often related to a number of factors including the size of the primary tumor, the location of the primary tumor within the breast, and the extent of auxiliary lymph node involvement.

It will be noted and appreciated, therefore, that for purposes of the present diagnostic methodology, primary human breast tumors of any kind, type, grade, age, size, stage, or cell origin may be sampled, utilized, and tested as specimens in order to determine whether or not that primary tumor is now or is soon to be metastatic. In most instances, a malignant breast tumor specimen (frozen or freshly obtained) from a primary tumor will be tested. In addition, should the physician or surgeon desire a diagnostic confirmation that a putative benign breast tumor clinically found in a living patient is truly noninvasive and will not metastasize, the present diagnostic methodology can and will serve as a confirmatory test procedure.

II. The nmt55 Protein and the DNA Expressing this Protein In-Vivo

The nmt55 protein and the genomic oligonucleotides coding for and expressing the protein in-vivo have only incidentally been identified in the scientific literature. The mere existence of such a 55 kDa nuclear protein was observed and first reported in Traish et al., 75th Annual Meeting of Endocrine Society, Programs and Abstracts P.157, Abstract 1863, 1993; and Traish et al., *Steroids* 61: 549–556, 1996. These publications merely identify the existence of the protein without providing any substantive characterization, much less functional value, to the reader.

The present invention relies upon detecting the presence or absence of the nmt55 protein as a diagnostic indicator for the first time in this art; and also provides the complete complementary DNA (cDNA) sequence from which the putative RNA sequence of bases may be immediately deduced and identified. Each of these will be described in detail individually below.

A. The nmt55 kDa Protein

The protein to be detected for diagnostic purposes is the nmt55 protein whose properties and chemical characteristics are as follows:

(a) The nmt55 protein is exclusively a nuclear binding protein which is found associated with the nuclei of normal and non-metastatic primary tumor cells. As shown experimentally hereinafter, a variety of normal tissues and cells express this particular protein; however, only those breast tumor cells which are not now and are not likely to be metastatic in nature will continue to express this nmt55 protein.

Figure 1:
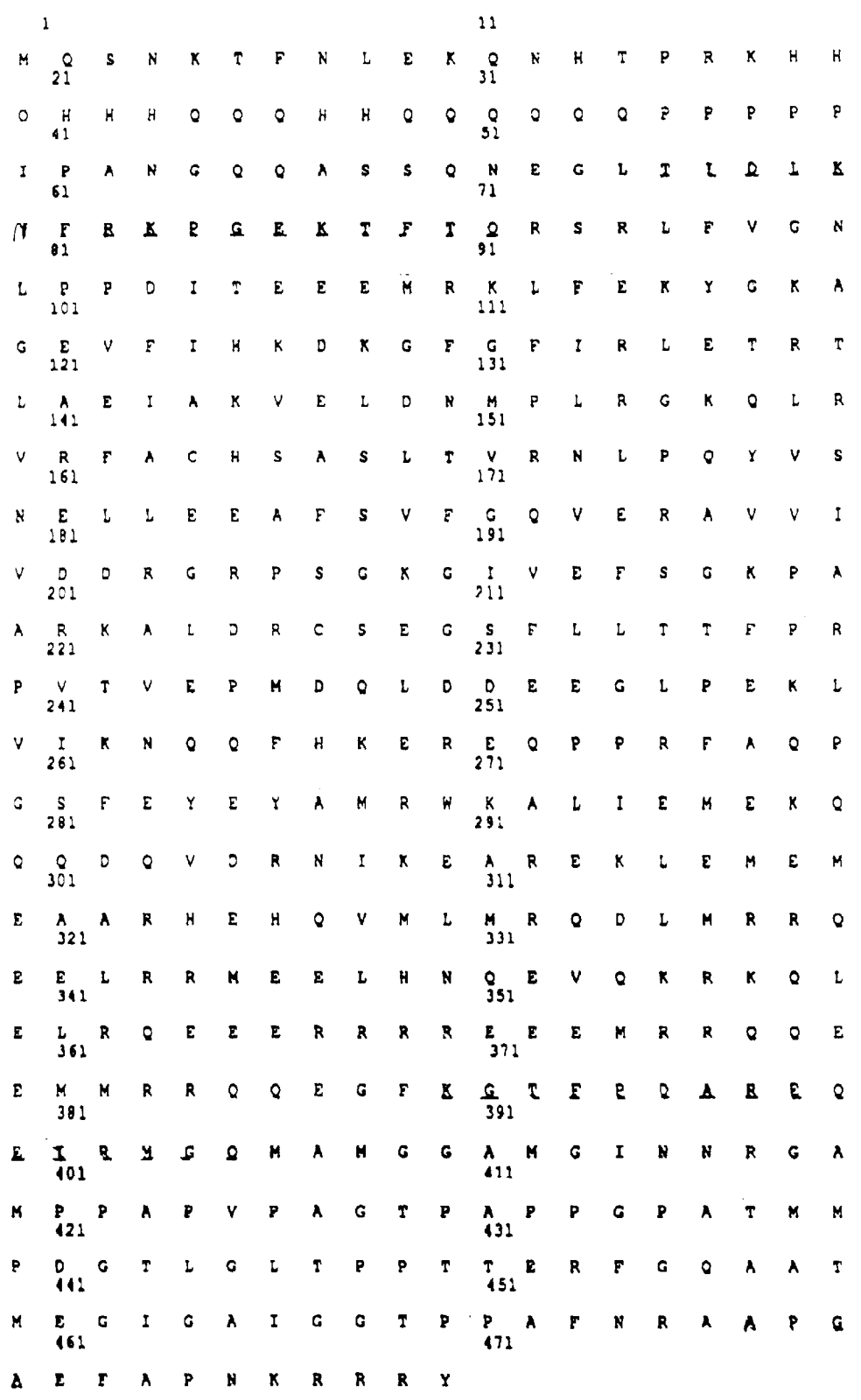

(b) The detected protein is approximately 55 kilodaltons in molecular weight. It has been found to be composed of 471 amino acid residues, the exact composition of which is recited by FIG. 1 herein. In addition, based on the empirical data, the nmt55 protein has a calculated molecular mass of 54,169 daltons. Thus, the empirical data showing the detected protein to be approximately 55 kDa in size is both accurate and precise.

(c) The nmt55 protein to be used as a marker comprises unique regions which are rich in glutamine, histidine, arginine, and glumatic acid. This is shown by FIG. 1.

(d) The nmt55 protein is not a proteolysed form of nuclear estrogen receptor protein; and the nmt55 protein is not part of or derived from any part of the estrogen receptor site. In addition, the nmt55 protein does not have any estradiol binding activity at all; and thus has no affinity as a steroid or a hormone.

(e) The nmt55 protein is coded for by its own genomic DNA and is expressed by translation of its own unique mRNA. The empirical studies presented hereinafter demonstrate a unique DNA oligonucleotide and unique RNA base sequence within cells which is unlike any other known to date.

In addition, the nmt55 protein employed as an indicator and marker for metastatic tumor cells has several other unique distinguishing properties. These include: (1) An absence of nmt55 protein expression which is significantly associated with mean tumor size; mean estrogen receptor status; and mean progesterone receptor status. (2) An absence of nmt55 protein expression which is not significantly associated with tumor stage, tumor grade, or tumor type. (3) An absence of nmt55 protein expression is extremely strongly associated with tumor hormonal phenotype; there is a total absence (100%) of the nmt55 protein in tumors which ER+/PR−; ER−/PR+; and ER−/PR−.

B. The DNA Expressing the nmt55 Protein

The complete cDNA base sequence coding and expressing the nmt55 protein in-vivo is recited by FIG. 2. In addition, several characteristics regarding the cDNA are experimentally demonstrated and include the following: (a) the DNA coding for the nmt55 protein, when present, exists only as a single copy and appears as a single unique gene within the genomic material of the cell; (b) the DNA identified by FIG. 2 yields a 2.6 kilobase cellular mRNA in-vivo; (c) the chromosomal mapping data locates the DNA expressing the nmt55 gene solely at the X chromosome, region q 13. Experiments and empirical data demonstrating and proving these attributes and characteristics are provided hereinafter.

III. Evidence of Clinical Utility and Diagnostic Operability for the Invention Clinically loss of ER expression and/or function has been found to correlate with poor tumor differentiation and possible tumor metastases [McGuire et al., "Predicting hormone responsiveness in human breast cancer", in *Estrogen Receptors In Breast Cancer* (McGuire, Carbone & Vollmer, editors), Raven Press, N.Y., 1975, pp. 17–30; McGuire et al., *Breast Cancer Res. & Treat.* 10: 5–9 (1987); McGuire, W. L., *Semin. Oncol.* 5: 528–433 (1978)]. Similarly, tumor size has been clinically viewed as a reliable indicator for the probability of metastatic dissemination of primary tumors [Koscienly et al., *Br. J. Cancer* 49: 709–715 (1984)].

To demonstrate diagnostic utility and clinical value for the present methodology, human breast cancer tissue was obtained from 76 patients undergoing surgery for treatment of breast cancer. These specimens were analyzed and evaluated for nmt55 proteins, ER, and PR status; and most (63 patients) were then evaluated for tumor size, tumor age and tumor stage and type.

A. Correlation with Tumor Cell ER Status

Estrogen and Progesterone Receptor Assays

The concentrations of unoccupied ER and PR of breast cancer tumor cells were determined by ligand binding analyses as described previously in the scientific literature. [See for example, Traish et al., *Diagnostic Molecular Pathology* 4: 220–228 (1995); Traish et al., *Steroids* 60: 467–474 (1995); Traish et al., *Steroids* 59: 362–370 (1994); and Traish et al., *Endocrinology* 118: 1327–1333 (1986).]

Western blot assay for presence of nmt55 protein

Nuclei from thirteen human breast tumors were individually extracted with 0.4 M KCl; electrophoresed in SDS/PAGE; transferred into nitrocellulose membrane; and analyzed with MAb#NMT-1 which is specific for nmt55 protein. The result is shown by FIG. 3.

Lanes 2–14 of FIG. 3 represent the different tumors, while lane 1 is the positive control using calf uterine nuclei extract. Subsequently, sixty three more tumors specimens were then tested the same way. The results of all 76 different human breast tumor test specimens tested by Western blot analysis are shown and summarized by Tables 1 and 2 below.

Table 1: Summary of Western blot data in testing 76 human breast tumor nuclei extracts for the expression of nmt55 kDa protein

TABLE 1

Summary of Western blot data in testing 76 human breast tumor nuclei extracts for the expression of nmt55 kDa protein

| Tumor ID # | nmt55 kDA Protein Presence | ER [fM/mg.] Protein | ER Presence | PR [fM/mg] Protein | PR Presence |
|---|---|---|---|---|---|
| 8152 | − | 50 | + | 0 | − |
| 8153 | − | 63 | + | 20 | + |
| 8154 | − | 130 | + | 1086 | + |
| 8155 | + | 165 | + | 1055 | + |
| 8156 | − | 4 | − | 0 | − |
| 8157 | − | 0 | − | 21 | + |
| 8158 | − | 63 | + | 9 | + |
| 8159 | − | 92 | + | 259 | + |
| 8160 | − | 25 | + | 0 | − |
| 8161 | − | 323 | + | 41 | + |
| 8162 | − | 0 | − | 6 | + |
| 8163 | − | 192 | + | 2 | + |
| 8164 | − | 1 | − | 3 | + |
| 8165 | − | 331 | + | 9 | + |
| 8166 | − | 6 | − | 5 | + |
| 8167 | − | 10 | + | 65 | + |
| 8168 | − | 62 | + | 33 | + |
| 8169 | + | 17 | + | 24 | |
| 8170 | + | 200 | + | 131 | + |
| 8173 | − | 3 | − | 0 | − |
| 8175 | − | 41 | + | 158 | + |
| 8177 | − | 12 | + | 53 | + |
| 8179 | + | 101 | + | 93 | + |
| 8180 | + | 196 | + | 768 | + |
| 8181 | + | 30 | + | 328 | + |
| 8182 | + | 65 | + | 509 | + |
| 8184 | − | 264 | + | 550 | + |
| 8185 | − | 73 | + | 38 | + |
| 8186 | − | 0 | − | 3 | + |
| 8187 | − | 79 | + | 333 | + |
| 8189 | − | 195 | + | 0 | − |
| 8190 | − | 3 | − | 0 | − |
| 8191 | − | 248 | + | 135 | + |
| 8192 | − | 1 | − | 3 | + |
| 8193 | + | 93 | + | 520 | + |
| 8195 | − | 153 | + | 619 | + |
| 8196 | − | 90 | + | 459 | + |
| 8197 | − | 22 | + | 10 | + |
| 8199 | − | 6 | − | 21 | + |
| 8201 | − | 24 | + | 12 | + |
| 8202 | − | 5 | − | 7 | + |
| 8203 | − | 9 | − | 28 | + |
| 8204 | − | 100 | + | 62 | + |
| 8205 | − | 53 | + | 84 | + |
| 8206 | − | 64 | + | 69 | + |
| 8207 | − | 194 | + | 9 | + |
| 8208 | − | 430 | + | 1591 | + |
| 5209 | + | 38 | + | 59 | + |
| 8211 | − | 3 | − | 0 | − |
| 8212 | + | 13 | + | 68 | + |
| 8213 | + | 40 | + | 55 | + |
| 8214 | − | 8 | − | 25 | + |
| 8215 | − | 5 | − | 1 | − |
| 8216 | − | 5 | − | 0 | − |
| 8217 | − | 13 | + | 0 | − |
| 8218 | − | 5 | − | 2 | + |
| 8219 | − | 62 | + | 65 | + |
| 8251 | − | 5 | − | 0 | − |
| 8253 | − | 391 | + | 76 | + |

TABLE 1-continued

Summary of Western blot data in testing 76 human breast tumor nuclei extracts for the expression of nmt55 kDa protein

| Tumor ID # | nmt55 kDA Protein Presence | ER [fM/mg.] Protein | ER Presence | PR [fM/mg] Protein | PR Presence |
|---|---|---|---|---|---|
| 8254 | − | 71 | + | 191 | + |
| 8255 | − | 458 | + | 320 | + |
| 8256 | + | 150 | + | 443 | + |
| 8257 | − | 40 | + | 259 | + |
| 8258 | − | 137 | + | 1 | − |
| 6259 | + | 251 | + | 339 | + |
| 8260 | − | 44 | + | 95 | + |
| 8261 | − | 0 | − | 0 | − |
| 8262 | − | 0 | − | 0 | − |
| 8263 | − | 2 | − | 0 | − |
| 8264 | − | 296 | + | 193 | + |
| 8265 | − | 4 | − | 2 | + |
| 8266 | + | 132 | + | 967 | + |
| 8267 | − | 35 | + | 16 | + |
| 8269 | − | 75 | + | 329 | + |
| 8272 | − | 102 | + | B3 | + |
| 8274 | + | 448 | + | 614 | + |

TABLE 2

| Tumor Category Status | Category Number (Percentage) of Total Tested | Presence of nmt55 Protein (+) | Absence of nmt55 Protein (−) |
|---|---|---|---|
| ER+/PR+: | | | |
| Empirical No. | 49/76 | 15/49 | 34/49 |
| Percentage | 65% | 31% | 69% |
| ER+/PR−: | | | |
| Empirical No. | 5/76 | 0/5 | 5/5 |
| Percentage | 6.6% | 0% | 100% |
| ER−/PR+: | | | |
| Empirical No. | 12/76 | 0/12 | 12/12 |
| Percentage | 16% | 0% | 100% |
| ER−/PR−: | | | |
| Empirical No. | 10/76 | 0/10 | 10/10 |
| Percentage | 13% | 0% | 100% |

It is recognized that both estrogen receptors and progesterone receptors are considered to be excellent and reliable tumor markers used in clinical prognosis of breast cancer patients. However, fully 35% of patients with a ER+ tumor status (without regard to PR status) of the breast fail clinically to respond to hormonal treatments and interventions.

The empirical data summarized within Tables 1 and 2 respectively correlates well with long-recognized clinical observations and ER/PR status of primary breast cancer tumors. As empirically shown, the nmt55 protein is always absent in ER negative tumor cells; is always absent from PR negative tumors; and is also absent in about ⅔ of all ER+/PR+ tumors. Conversely, the nmt55 protein marker is present in only about ⅓ of ER+/PR+ breast tumors. In short, all ER− breast cancer tumors tested showed an absence of nmt55 protein [regardless of the PR status of the tumor cells]. The absence of the nmt55 protein is thus a reliable marker and operative clinical indicator that the tumor in the breast is now or is soon likely to be metastatic.

B. Statistical Correlations

Of the available human breast cancer tumor specimens, 63 had pathological report data concerning tumor size, tumor stage, tumor grade, and tumor type. Of these, tumor size has been viewed as an emphatic indicator for the probability of metastatic dissemination of a primary breast cancer tumor. Accordingly, 63 human breast tumor cell specimens (of the original 76 test samples) were statistically evaluated to determine their relationships on the basis of tumor size, grade and age as well as ER and PR expression.

Statistical analyses were performed to determine the association between nmt55 protein expression, ER and PR expression, and tumor pathological characteristics. Two-sample t-test procedures were used to compare the mean values of ER and PR concentrations and tumor size with presence or absence of nmt55 protein. Chi square analyses were also conducted to examine possible differences between tumor characteristics (stage, grade, tumor hormonal phenotypes and tumor type) and nmt55 protein status. Multiple logistic regression analyses were performed to assess the association of nmt55 presence with ER and PR concentrations, adjusting for tumor characteristics. All statistical analyses were performed using mainframe SAS version 6.11 at Boston University. The statistical results are summarized by Table 3 below.

TABLE 3

Statistical Analyses
Variable: T SIZE

| Protein | N | Mean | Std Dev | Std Error |
|---|---|---|---|---|
| yes | 21 | 1.76190476 | 0.83455149 | 0.18211407 |
| no | 38 | 2.71051632 | 2.47307550 | 0.40118582 |

| Variances | T | DF | Prob >|T| |
|---|---|---|---|
| Unequal | −2.1531 | 49.9 | 0.0562 |
| Equal | −1.6994 | 57.0 | 0.0947 |

For HO: Variances are equal, F' = 8.78   DF = (37, 20)
Prob > F' = 0.0000

Variable: T GRADE

| Protein | N | Mean | Std Dev | Std Error |
|---|---|---|---|---|
| yes | 18 | 2.22222222 | 0.64676167 | 0.15244319 |
| no | 29 | 2.24137931 | 0.686947042 | 0.12803144 |

| Variances | T | DF | Prob >|T| |
|---|---|---|---|
| Unequal | −0.0962 | 38.0 | 0.9238 |
| Equal | −0.0948 | 45.0 | 0.9249 |

For HO: Variances are equal, F' = 1.14 DF = (28, 17)
Prob > F' = 0.7999

Variable: T AGE

| Protein | N | Mean | Std Dev | Std Error |
|---|---|---|---|---|
| yes | 23 | 63.26086957 | 12.76435873 | 2.66155278 |
| no | 40 | 60.50000000 | 17.3560096 | 2.74422470 |

| Variances | T | DF | Prob > |T| |
|---|---|---|---|
| Unequal | 0.7222 | 57.2 | 0.4731 |
| Equal | 0.6655 | 61.0 | 0.5083 |

For HO: Variances are equal, F' = 1.85   DF = (39, 22)
Prob > F' = 0.1270

Variable: ER

| Protein | N | Mean | Std Dev | Std Error |
|---|---|---|---|---|
| yes | 23 | 164.60869565 | 149.08531393 | 31.08643688 |
| no | 40 | 42.32500000 | 78.39393864 | 12.39517004 |

| Variances | T | DF | Prob > |T| |
|---|---|---|---|
| Unequal | 3.6539 | 29.1 | 0.0010 |
| Equal | 4.2756 | 61.0 | 0.0001 |

TABLE 3-continued

For HO: Variances are equal, F' = 3.62  DF = (22, 39)
Prob > F' = 0.0005

Variable: PR

| Protein | N | Mean | Std Dev | Std Error |
|---|---|---|---|---|
| yes | 23 | 344.17391304 | 352.01648362 | 73.40051082 |
| no | 40 | 23.37500000 | 53.24914228 | 8.41942865 |

| Variances | T | DF | Prob > \|T\| |
|---|---|---|---|
| Unequal | 4.3421 | 22.6 | 0.0002 |
| Equal | 5.6848 | 61.0 | 0.0000 |

For HO: Variances are equal, F' = 43.70  DF = (22, 39)
Prob > F'= 0.0000

Variable: RATIO pr/er ratio

| Protein | N | Mean | Std Dev | Std Error |
|---|---|---|---|---|
| yes | 23 | 3.68162484 | 5.40966574 | 1.12799328 |
| no | 16 | 1.15142010 | 1.55509419 | 0.38877355 |

| Variances | T | DF | Prob > \|T\| |
|---|---|---|---|
| Unequal | 2.1207 | 27.0 | 0.0435 |
| Equal | 1.8129 | 37.0 | 0.0780 |

For HO: Variances are equal, F' = 12.10  DF = (22, 15)
Prob > F' = 0.0000

Tumor Pathological Characteristics

The tumor data analyzed from the 63 patients who underwent surgery for treatment of breast cancer also showed the following characteristics: The mean age of the patients was 61.5 years (SD±15.8) with a range of 30–95 years. The racial composition of the patients was 40 (63.5%) white, 4 (3.2%) black, two (4.3%) Hispanic and 18 (28.6%) of unknown race. Fifty two out of 62 tumor specimens (83.9%) were characterized as infiltrating ductal carcinoma; six (9.7%) were infiltrating lobular carcinoma; two (3.2%) were ductal carcinoma in situ; and one (1.6%) lobular carcinoma in situ; and one was inflammatory. The distribution of tumors based on size was as follows: 3.4% was between 0–0.9 cm; 52.5% between 1–1.9 cm; 33.9% between 2–4.9 cm.; and 10.2% were 5 cm or greater. Tumor stage and grade were available for 48 and 47 of the 63 patients, respectively. Approximately 44% of tumors were stage I, 33% were stage IIA or IIB, and 22.9% were stage IIIA or higher. Six out of 47 tumors were classified as grade 1, 24 were classified as grade 2 and 17 were classified as grade 3. Summaries of this data are presented by Tables 4 and 5 below.

Expression of ER, PR and nmt55 Protein in Human Breast Tumors

The pathology records of these 63 patients (as discussed above) were also statistically analyzed to determine if nmt55 protein is associated with expression of the biochemical markers ER and PR and some pathological characteristics. All tumors which expressed nmt55 were ER+(100%), whereas 60% of tumors lacking nmt55 were ER+(p=0.001). Similarly, all tumors expressing nmt55 were PR+(100%) compared to 62.5% of tumors (PR+) in which nmt55 was absent (p=0.001). The mean tumor size was significantly greater (mean=2.7 cm) in tumors lacking nmt55 protein, than those in which nmt55 was present (mean=1.8 cm) (p=0.036). The tumor hormone phenotype varied signifi cantly by hormone status (p=0.001) and all tumors expressing nmt55 were ER+/PR+. Of tumors lacking nmt55 protein, 40% were ER+/PR+; 20% were ER+/PR−; 17.5% were ER−/PR−; and 22.5% were ER−/PR+. A summary of this data is presented by Tables 6 and 7 below.

TABLE 4

Demographics of Sample Population (N = 63 women)

| Race | Number (%) |
|---|---|
| White | 40 (63.5%) |
| Black | 4 (6.4%) |
| Hispanic | 2 (3.2%) |
| Unknown | 18 (28.6%) |

Mean Age (N=63): 61.5 years SD=15.78, Range (30–95 years)

TABLE 5

Tumor Characteristics

|  | Number (%) |
|---|---|
| Tumor Stage: |  |
| 1 | 21 (43.8) |
| 2a–2b | 16 (33.3) |
| 3a–4 | 11 (22.9) |
| N = 48 |  |
| Tumor Grade: |  |
| 1 | 6 (12.9) |
| 2 | 24 (51.1) |
| 3 | 17 (36.3) |
| N = 47 |  |
| Tumor Type: |  |
| Infiltrating Ductal | 52 (83.9) |
| Infiltrating Lobular | 6 (9.7) |
| DCIS* | 2 (3.2) |
| LCIS* | 1 (1.6) |
| Inflammatory | 1 (1.6) |
| N = 62 |  |
| Tumor Size: |  |
| 0–0.9 | 2 (3.4) |
| 1–1.9 | 31 (52.5) |
| 2–4.9 | 20 (33.9) |
| >5.0 | 6 (10.2) |
| N = 59 |  |

*DCIS: Ductal carcinoma in-situ
**LCIS: Lobular carcinoma in-situ

TABLE 6

Estrogen, Progesterone, and Nuclear Protein (nmt55) Tumor Status

|  | Number (%) |
|---|---|
| Tumor Hormone Phenotype: |  |
| ER+/PR+ | 39 (61.9) |
| ER+/PR− | 8 (12.7) |
| ER−/PR− | 7 (11.1) |
| ER−/PR+ | 9 (14.3) |
| N = 63 |  |
| Presence of nmt55 protein: |  |
| Yes | 23 (36.5) |
| No | 40 (63.5) |
| N = 63 |  |

TABLE 7

A. Pearson Correlation Analysis for Nuclear Protein Status:
(Statistical significance was determined at the alpha level of 0.05)

|  | Correlation Coefficient | p Value |
|---|---|---|
| 1. ER concentration | −0.48019 | 0.0001 |
| 2. PR concentration | −0.58848 | 0.0001 |
| 3. Hormone Status* | 0.52705 | 0.0001 |
| 4. Age | −0.08 | 0.508 |
| 5. Nuclear nodes | −0.13775 | 0.3558 |

*Hormone status refers to the combined ER and PR status of the tumor

B. Chi-Square Analysis:

|  | Nuclear Protein Presence | | |
|---|---|---|---|
|  | Yes (n = 23) | No (n = 40) | p |
| ER Status: | | | |
| ER− | 0% | 40 | 0.001 |
| ER+ | 100 | 60 | |
| PR Status: | | | |
| PR− | 0% | 37.5% | 0.001 |
| PR+ | 100 | 62.5 | |
| Tumor size (cm)* | 1.8 (0.8) | 2.7 (2.5) | 0.036 |
| ER (fmol)* | 164.6 (149.1) | 42.3 (78.4) | 0.001 |
| PR (fmol)* | 344.2 (352.0) | 23.4 (53.2) | 0.002 |
| ERPR Phenotype | | | |
| ER+/PR+ | 100% | 40.0% | 0.001 |
| ER+/PR− | 0 | 20.0 | |
| ER−/PR− | 0 | 17.5 | |
| ER−/PR+ | 0 | 22.5 | |

*Mean (s.d)

C. Summary of Evidence

A 55 kDa nuclear protein (referred to as nmt55) from human breast tumors is identified and characterized as a marker for metastatic tumor cells. Measurements of estrogen (ER) and progesterone (PR) receptors, by ligand binding assays, in cytosols of 63 human breast tumors permitted classifications of these tumors into four phenotypes (ER+/PR+, ER+/PR−, ER−/PR−, ER−/PR+). nmt55 protein expression in these tumors, as determined from Western blot analyses, showed a statistically significant association (p=0.001) with tumor hormonal phenotype. Review of the pathological characteristics of tumors analyzed suggested that lack of nmt55 expression was significantly associated with mean tumor size (p<0.03), mean ER (p=0.001) and mean PR (p<0.002), but was not associated with tumor stage, grade or type.

IV. Assays to Detect the nmt55 Protein in Tumor Cells

The preferred mode of diagnostic method to detect the nmt55 kDa protein in a cellular test sample is via the use of specific antibodies and established immunoassay procedures. A detailed description of suitable antibodies, monoclonal and polyclonal, as well as their various structures and formats, modes of preparation, and manner of intended use is summarized below.

A. Antibodies Specific for the nmt55 Protein

The antibodies and antisera suitable for use in the present diagnostic methodology must demonstrate the capability of binding to at least one epitope of nmt55 protein. However, this binding capability can be demonstrated not only by a whole intact antibody, but also by F(ab')$_2$ fragments, and also by Fab fragments derived from the whole antibody structure. It will be recalled that while the whole antibody is a large bulky protein having two binding sites, the F(ab')$_2$ fragment represents a divalent binding fragment of the whole antibody; while the Fab binding portion is a univalent binding unit having a minimum of antibody structure. In addition, smaller and genetically engineered antibody units having a specific binding capability have also been developed as reported in the scientific literature; and these are deemed to be equally suitable for use herein. Methods for preparing, isolating, and purifying each of these different antibody binding segments and units are conventionally known in the scientific literature and have been available for many years as common knowledge in this field. The user may thus chose from among all of these different whole antibodies, antibody subunits and antibody fragments in picking a useful entity and structure having a specific binding capability for an epitope of nmt55.

In addition, the user has the option to chose whether the antibody is obtained from monoclonal, or polyclonal or broad antisera sources. Equally important, the user will decide whether the source of antibody or antibody fragments should be isolated and purified prior to use; or whether the antibody containing medium can be employed as a heterogeneous mixture of different entities and varying binding affinities, only some of which will have the requisite affinity and specific binding capability for an exposed epitope of nmt55 protein. Thus, the degree of homogeneity of purity, binding and affinity and specificity of antibodies or antibody fragments and genetically engineered subunits for one or more epitope of bound VPF is left to the discretion and needs of the user.

It will be noted and appreciated also that each nmt55 protein molecule shown by FIG. 1 provides a large number of potential antigenic determinants for use. Thus when choosing an immunogen, it will be recalled that a minimum of 5–7 amino acid residues (in theory) are able to be employed as a haptene in order to raise specific antibodies within a living host animal. However, longer peptide lengths of 10–20 residues are generally preferred. It will be noted also that the different regions which can be used as a source of antigenic determinants each provide far longer amino acid residue segments for this purpose. Thus, even if an extended segment length of 10–20 amino acid residues were purposely employed as the immunogen, a large number of different antigenic determinants becomes available given the range of residue choices provided by nmt55 protein. Accordingly, with the choice of many different and lengthy region segments to the user, the number of potential epitopes becomes enormous; yet each of these epitopes is a potential specific binding site for the antibody binding portion of the conjugate molecule.

Immunogens

It is intended and envisioned that at least one peptide segment representative of nmt55 protein (FIG. 1) of suitable length (preferably 10–20 residues) be chosen as the immunogen in order to provide the antigenic determinants and the production of specific antibodies using a living host animal. Once the amino acid residue length and composition has been chosen, the chosen antigenic or haptene segment must be prepared. Preferably, the desired amino acid segment is synthetically prepared using conventionally known solid phase peptide synthesis methods [such as Merrifield, R B, J. Am. Chem. Soc. 85: 2159 (1963)]. Once synthesized, it is most desirable that the chosen segment be purified (such as by gel filtration) and desirably analyzed for content and purity (such as by sequence analysis and/or mass spectroscopy).

After its synthesis, the chosen segment is desirably coupled with a protein carrier to form the immunogen. Conventionally suitable protein carriers available for this purpose are available in great variety from many diverse sources. The only requirements regarding the characteristics and properties of the carrier are: first, that the protein carrier be in fact antigenic alone or in combination with the synthesized chosen amino acid residue sequence; and second, that the carrier protein be able to present the antigenic determinants of the residue sequence such that antibodies specific against the amino acid residues are produced in a living host animal. Clearly, as the experiments described hereinafter, the preferred choice of protein carrier for immunization purposes include keyhold limpet hemocyanin (KLH), coupled by glutaraldehyde (GLDH), sulfo-m-maleimidobenzo (M-hydroxysuccinimide) ester (MBS), or bisdiazobenzidine (BDB). However, any other carrier protein compatible with the host to be immunized is also suitable for use. Examples of such other carrier proteins include bovine serum albumin, thyroglobulin, and the like.

Immunization Procedure

All immunizations and immunization procedures are performed in the conventionally known manner described in the scientific literature. It is expected that under certain use conditions, adjuvants will be employed in combination with the prepared immunogens. Alternatively, the prepared immunogens may be used alone and be administered to the animal or human host in any manner which will initiate the production of specific antibodies.

In addition, the harvesting of polyclonal antiserum and the isolation of antibody containing sera or antibody producing cells follows the conventionally known techniques and processes for this purpose. Similarly, the preparation of hybridomas follows the best practices developed over recent years for the isolation of monoclonal antibodies [Marshak-Rothstein et al., *J.Immunol.* 122: 2491 (1979)].

Polyclonal and Monoclonal Antibodies

Once obtained, the polyclonal antisera and/or monoclonal antibodies and/or genetically engineered antibodies should be evaluated and verified for their ability to bind specifically with an epitope existing within a spatially exposed region of nmt55 protein. Also, cleavage with papain will produce two Fab fragments plus the Fc fragment; whereas cleavage of the antibodies with pepsin produces the divalent $F(ab')_2$ fragment and the Fc' fragment—all as conventionally known.

It will be expressly understood, however, that regardless of whether the antibody binding portion represents polyclonal antisera, monoclonal antibodies, the $F(ab')_2$ fragment, Fab fragments, or other antibody subunits—all of these are suitable and intended for use so long as the specific binding capability is demonstrated for at least one epitope within nmt55 protein. It is therefore deemed conventional and expected that a wide variety of different immunoassay systems may be employed to utilize the specific binding capability of the antibody with the present invention; and that the parameters of concentration, volume, temperature and choice of reagents can be varied extensively at will in the choice of antibodies and/or antibody fragments and subunits employed for this purpose. The present invention therefore presumes and incorporates by reference any conventionally known immunoassay technique, procedure, protocol, or other non-decisive factor or parameter—all of which may be usefully employed for the present invention via a specifically binding antibody.

B. The NMT-1 Polyclonal and Monoclonal Antibodies

Preferred polyclonal antisera and monoclonal antibodies suitable for use in the present diagnostic test method were raised against a haptene originating in the A/B region of human estrogen receptor (hER) encompassed by amino acid residues at position nos. 1–184 in the native hER protein. The haptene itself is limited in content and represents only the segment of amino acid residues from positions nos. 140–154 of the native A/B region of hER. This NMT-1 oligopeptide segment is constituted as:

Thr-Val-Arg-Gly-Ala-GlN-Pro-Pro-Ala-Phe-Tyr-Arg-Pro-Asn-Ser

It will be noted and appreciated that while the nmt55 protein is itself not part of or derived from the ER receptor protein of human estrogen sensitive cells, it is nevertheless true and accurate that an antibody having a specificity for the A/B region of hER is cross-reactive with and specifically binds to the nmt55 kDa non-receptor protein (solubilized by extraction of nuclei from human breast cancer tumor cells). This antibody cross-reactivity and specificity has been previously described and reported in the scientific literature as an incidental observation. These published reports include: Traish et al., 75th Annual Meeting of Endocrine Society, Programs and Abstracts, Abstract No. 1863, 1993; and Traish et al., *Steroids* 59: 362–370 (1994). See also Traish et al., *Steroids* 61: 549–556 (1996) for more detailed information regarding the use of these antibodies against epitopes in the A/B region of human estrogen receptors. The texts of all of these publications are expressly included by reference herein.

Synthesis of Oligopeptides

The oligopeptide NMT-1 was prepared using conventionally known solid phase peptide synthesis methods [Merrifield, R. B., *J. Am. Chem. Soc.* 85: 2149 (1963)]. Once synthesized, the individual oligopeptides were purified by gel filtration and analyzed for purity by HPLC. Analysis of the amino acid composition correlated well with the primary sequence. Each peptide contained one [$^3$H]-labeled amino acid as a tracer. This provided the means for determining the efficiency of coupling to the various carrier proteins.

Immunization of Mice

Groups (four animals/group) of female mice [BALB/cA/J) $F_1$] 6–8 weeks old were also immunized by injecting s.c. 100 μg of the NMT-1 oligopeptide, emulsified in Freund's complete adjuvant. Two s.c. booster injections were given at 3 week intervals. The mice were bled through the vein and the sera were tested for antibodies by sucrose density gradient analysis.

Polyclonal Antisera Production

The immunogen and the raising of antisera did show some variation among the host animals (6 mice per group). Positive polyclonal antisera, as determined by sucrose density gradient analysis were obtained against all peptides, however, the response rate was different for animal. All the mice (6 per group) immunized with peptide NMT-1 produced positive polyclonal antisera.

Specific Monoclonal Antibodies The polyclonal antibodies to peptide NMT-1 were shown to cross-react with the nmt55 nuclear protein that was present mainly in ER+ breast tumors. For this reason, monoclonals to peptide NMT-1 were obtained. Five clones were isolated but only two were characterized, NMT-1-C6 and NMT-1-E7. These were characterized with respect to their ability to recognize the nmt55 protein.

Results

Five monoclonal antibodies were developed against peptide NMT-1 (amino acids 140–154 of hER). These monoclonal antibodies were found to be receptor-specific and exhibited all the characteristics described for the polyclonal antisera raised against this peptide. Western blot analysis demonstrated that each of the five monoclonal antibodies recognized a 55 kDa protein extracted from nuclei of estrogen target tissues and from human breast tissue samples that were shown to contain cytoplasmic estrogen receptor by ligand binding assays. The monoclonal antibodies recognized the estrogen receptor in immunocytochemical assay using human breast tissue and in rat uterine tissue. The monoclonal antibodies to NMT-1 oligopeptide also detect a nmt55 nuclear protein in the MCF-7 cell line (a human breast cancer cell line).

V. Assays to Detect RNA and DNA Coding for nmt55 Protein in Cells

Many techniques for manipulating and modifying RNA and DNA oligonucleotides have been reported and are today widespread in use and in application. Merely exemplifying the many authoritative texts and published articles presently available in the literature regarding uses of DNA and RNA, gene expression, and genetic analyses are the following: *Gene Probes for Bacteria* (Macario and De Macario, editors) Academic Press Inc., 1990; *Genetic Analysis, Principles Scope and Objectives* by John R. S. Fincham, Blackwell Science Ltd., 1994; *Recombinant DNA Methodology II* (Ray Wu, editor), Academic Press, 1995; *Molecular Cloning, A Laboratory Manual* (Maniatis, Fritsch, and Sambrook, editors), Cold Spring Harbor Laboratory, 1982; *PCR (Polymerase Chain Reaction)*, (Newton and Graham, editors), Bios Scientific Publishers, 1994; and the many references individually cited within each of these publications.

Among the many innovative procedures and novel techniques generated by molecular research studies has been the use of nucleic acid probes for identifying the existence of specific DNA and RNA and the products of oligonucleotide expression. These techniques are directly applicable for the diagnostic detection of DNA and/or RNA coding for the nmt55 kDa protein within the cells of a primary human breast cancer tumor originating from a living human patient.

A. Probes for Detecting nmt55 DNA and RNA Oligonucleotide Targets

By definition, a nucleic acid probe is a DNA or RNA oligonucleotide fragment of known base sequence which exists as a single-stranded segment of base codons. A nucleic acid probe suitable for the present method will thus selectively bind to a complementary base sequence—tumor cell nmt55 DNA or RNA—the analyte of interest in the diagnostic test. Thus, an nmt55 oligonucleotide probe, via its selective binding capability, can be employed to detect and identify individual complementary nucleic acid sequences coding for the nmt55 kDa protein present in primary human breast cancer tumor cells which serve as samples for diagnostic testing.

In general, any nmt55 DNA (or RNA) sequential fragment corresponding at least in part to that shown by FIG. 2 (obtained from any source and regardless of whether the sequence is naturally occurring or synthetically prepared) should meet two essential criteria in order to be truly useful as an olgionucleotide probe for the detection of nmt55 DNA and RNA in tumor cells. First, the oligonucleotide probe sequence must be as specific as possible for the intended complementary target—the nmt55 DNA or RNA; and, preferably, bind exclusively with only the intended complementary nmt55 oligonucleotide target sequence with little or no cross-reaction. Secondly, the nmt55 oligonucleotide probe must be able to distinguish among closely related nucleic acid base sequences having a substantial degree of homology as well as be able to bind selectively with varying types and sources of nucleic acid fragments having the complementary nmt55 oligonucleotide target sequence as part of its composition. Thus, the size or length of the nmt55 oligonucleotide probe and the repetitive nature of or copy number for the complementary nmt55 DNA or RNA target sequence will meaningfully affect not only the specificity, but the sensitivity of the nmt55 probe for detection purposes.

The nature of the nmt55 Oligonucleotide Probe

The oligonucleotide sequence chosen for use as a nmt55 probe may be obtained from any source; be prepared or purified in any manner; and vary in size or length without meaningful limit so long as it is representative of the DNA shown in FIG. 2. The chosen nmt55 nucleic acid sequence may be DNA or RNA in composition; may be endogenously or exogenously derived; may be naturally occurring or synthetically prepared; may be composed of a minimum number of nucleic acid bases; or be composed of many thousands of nucleotides in sequence. For example, the user may thus employ genomic or chromosomal DNA, plasmid DNA, and/or a cloned or replicated DNA which is representative of a nmt55 marker or sequence within a cell. Similarly, the oligonucleotide nucleic acid fragment utilized as a probe may represent or comprise nmt55 RNA in its many forms (such as messenger or transfer, or mitochondrial RNA) as it exists in nature or is synthetically produced. All of these diverse origins and sources of nucleic acid sequences are conventionally known; and many techniques for their individual preparation, isolation, and purification as single-stranded nucleic acid chains of known composition, sequence, and specific binding capabilities are available in the published literature today.

Regardless of the particulars regarding the nucleic acid sequence or fragment chosen for use as an nmt55 oligonucleotide probe, two essential requirements must be met and satisfied in every instance. First, the nmt55 nucleic acid segment should be of known composition and sequence order, and thus bind selectively and specifically with a tumor cell complementary oligonucleotide target sequence primarily, if not exclusively. The degree of selectivity and hybridization for the nmt55 oligonucleotide probe will thus vary with the specificity of its nucleic acid sequence and the degree of homology permitted among different and competing complementary target species. Thus, the more exact and controlled the nucleic acid sequence of the nmt55 probe, the more selective and specific the binding with complementary oligonucleotide target specie. Second, the nmt55 oligonucleotide probe must bind with its intended nmt55 oligonucleotide cellular target at each and every instance and occasion where the tumor cell complementary target species is presented for reactive contact. Thus, although the tumor cell complementary target sequence typically exists in a single copy number and/or may be encased in a larger-sized tumor cell oligonucleotide fragment containing non-complementary base sequences, the nmt55 oligonucleotide probe should nevertheless bind to the nmt55 targeted portion of these larger fragments when they come into reactive contact with the nmt55 probe. Such binding capacity provides both specificity and sensitivity for the diagnostic test method as a whole.

B. Identifying Labels for nmt55 Oligonucleotide Probes

In general, two categories of identifying labels exist which are useful with nmt55 oligonucleotide probes: radionuclides and light energy absorbing dyes. These are conventionally known and routinely employed in oligonucleotide hybridization assays; and the choice of which type of identifying label to use is typically left to the individual as a matter of convenience or personal preference.

Radionuclide Labels

A number of radioisotopes may be employed as an identifying label for the nmt oligonucleotide probes. These radionuclides emit specific particles or energy radiations which can be detected by radiography using conventionally known apparatus. A representative but non-exhaustive listing of radionuclides suitable for use as an identifying label with nmt55 probes is provided by Table 8 below.

The scientific literature is replete with protocols and procedures for attaching a radioisotope to a chosen oligonucleotide sequence. All of these conventionally known and routinely employed attachment techniques and procedures are deemed to be within the scope of the present invention.

TABLE 8

Radionucleotides

| Nuclide | Half-life | Decay Mode* |
|---|---|---|
| gaillum 67 | 78 hours | E.C. |
| gold-198 | 2.7 days | β- |
| indium-113m | 100 minutes | E.C. |
| iodine-123 | 13.3 hours | E.C. |
| iodine-125 | 60.0 days | E.C. |
| iodine-131 | 8.05 days | β- |
| mercury-197 | 65 hours | E.C. |
| technetium-99m | 6.0 hours | I.T. |
| thallium-201 | 73 hours | E.C. |
| xenon-133 | 5.3 days | β- |

Decay Modes: β- = beta decay; E.C. = electron capture
I.T. = isomeric transition Light Energy Absorbing Dyes Useful as Joined Identifying Labels At least one light energy absorbing dye can be bound initially or become linked subsequently to each nmt55 oligonucleotide fragment used as a probe. If desired, more than one of these dye reagents can be employed as a joined identifying label with a nmt55 probe.

Each light energy absorbing dye formulation or composition will be bound directly or become linked indirectly to the one fragment or to multiple different fragments of oligonucleotides corresponding to those shown by FIG. 2 and intended for use as a nmt55 probe. Moreover, each dye will then show evidence of its presence by either absorbing and reflecting light energy of a predetermined wave length; or, alternatively, by absorbing light energy and then subsequently emitting light energy of a different wavelength in return. Such reflected or emitted light energy is intended and expected to be detected and conveyed using conventionally known apparatus and systems for light energy detection and measurement.

The various dyes which may be bound initially or linked subsequently to a chosen nmt55 oligonucleotide fragment as a joined identifying label are all conventionally known and often commercially available. The present invention intends that all the commonly useful properties and capabilities of the various classes of light energy absorbing dyes be employed directly and indirectly as needed or desired for the specific use or application. Merely illustrative of the many different dyes are those fluorophores, indirect (secondary) labels, and interchelators listed below within Tables 9, 10 and 11 respectively.

TABLE 9

| Compounds | Excitation Wavelength (range or maximum) | Fluorescence emission range (max) |
|---|---|---|
| A. Fluorophores | | |
| Eosin | 520–530 nm | 530–580 nm (550 nm) |
| TRITC-amine | 555 nm | 570–619 nm (590 nm) |
| Quinine | 320–352 nm | 381-450 nm |
| Fluorescein W | 488-496 nm | 530 nm |
| Acridine yellow | 464 nm | 500 nm |
| Lissamine Rhodamine B Sulfonyl Chloride | 567 nm | 580 nm |
| Erythroscein | 504 nm | 560 nm |
| Ruthenium (tris, bipyridium) | 460 nm | 580 nm |
| Texas Red Sulfonyl Chloride | | |
| B-phycoerythin | 545, 565 nm | 575 nm |
| Nicotinamide adenine dinucleotide (NADN) | 340 nm | 435 nm |
| Flavin adenine dinucleotide (FAD) | 450 nm | 530 nm |
| Carboxy Seminaphthorhydafluor | 587 nm | 640 nm |
| Naphthofluorescein | 594 nm | 663 nm |
| Carboxy Fluorescein (Fam) | | |
| B. Fluorescent Antibody Conjugates | | |
| Protein A fluorescein conjugates | 480 nm | 520 nm |
| Anti-Atrazine fluorescein Conjugates | 480 nm | 520 nm |
| digoxin-Anti-digoxin Texas Red Conjugates | 590 nm | 615 nm |

TABLE 10

Secondary Label Pairs
(Labels include but are not limited to those mentioned in Table 1)

| | |
|---|---|
| Biotin | Labeled avidin/streptavidin |
| Protein A | Labeled IgG |
| Digoxin | Labeled anti-digoxin |
| Enzymes such as: | |
| alkaline phosphatase | diphosphate derivatives |
| β-glucuronidase | ELF-97 substrates |

TABLE 11

Interchelators ethidium bromide;
Cy-5;
Ru (byp)$_2$ MCCP;
Hoechst 33258 (bis-benzimide);
Cyanine dyes (for example, the Toto series SYBRI)

It will be recognized and appreciated also that the available range, variety, and diversity of light energy absorbing dyes, dye formulations, and dye mixtures is not dependent upon a single light source or light energy supply in order to be effective. Although light energy of determinable wavelengths is desirably provided by electrical light sources— that is, light emitting diodes (LEDs), lasers, laser diodes and filament lamps whose bands of light energy are typically controlled and selected by filters, diffraction gratings, polarized filters; or alternatively broken into various broad wavelengths of light energy via prisms, lenses, or other optical/spectral articles, these are not exclusively the only source of useful light energy. Clearly, in various applications and circumstances other less typical light energy sources will also be useful. Accordingly, neither the true source, nor the nature of light energy photons, nor the manner in which they are conveyed or otherwise caused to be created is of importance or consequence.

In addition, the dye label individually may comprise a pair of specifically binding materials such as the chemical compounds listed within Table 9 for subsequent reactive contact and indirect juncture of an identifying label. Thus each dye label individually may in fact be formulated as a composite comprising light emitting dye in part; and include a variety of receiving elements which are able to interact as specific binding partners for joining the light energy dye label subsequently. Exemplifying some multiple formulations and combinations are those described below.

Methods for Preparing a nmt55 Probe Bearing an Identifying Label

A range of different preparation methods and processes are conventionally known and available in the published scientific literature for creating a oligonucleotide probe of known base sequence joined directly to an identifying label as a conjugate. Representative of and exemplifying these direct attachment procedures are the following: Agrawal, et. al., *Nucleic Acids Res.* 14: 6227–6245 (1986); Smith et. al., *Nucleic Acids Res.* 13: 2399–2412 (1985); Cardullo et. al., *Proc. Natl. Acad. Sci. USA* 85: 8790–8794 (1988); *J. Fluorescence* 1: 135 (1991).

An alternative preparation strategy and procedure is exemplified by incorporation of biotin, in the form of a biotinylated nucleotide (such as biotin-d UTP), into the nucleic acid structure of the probe using conventional procedures such as nick translation or tailing [Rigby et. al., *J. Mol. Biol.* 113: 237 (1977); Lobban, P. E. and A. D. Kiser, Jr. *Mol. Biol.* 78: 453 (1973)]. The selective binding of the biotinylated target to the probes in the hybridization reaction may then proceed in the absence of the dye label itself. Subsequently a conjugate complex constituted of avidin or streptavidin (proteins with a high affinity for binding to biotin) covalently are linked to a fluorescent or color reflecting dye ligand is then added as a dye label complex to the reaction fluid after hybridization has occurred; and the selective binding capability for the paired agents will then cause the identifying dye label to be joined via the avidin (or streptavidin) indirectly to each biotinylated target species wherever it is found. Qualitative and quantitative optical detection of the hybridized target specie can therefore be made on the basis of the spectral characteristics of the ultimately and indirectly joined identifying label. The listing of Table 10 provides other alternative pairs of specific binding agents suitable for use.

If desired, a biotinylated oligonucleotide probe may be also prepared using polymerase chain reaction processing. The biotinylated amplified product obtained by PCR methodology may be used immediately or purified before being placed into reactive contact with the biosensor. Also, any of the other pairs listed in Table 9 may be substituted for use in the PCR method.

In addition, the user may optionally employ the technology known as enzyme-labeled fluorescence (ELF) signal amplification to provide a joined identifying label. This technology is described in detail by U.S. Pat. Nos. 5,136,906 and 5,443, 986, the texts of which are expressly incorporated by reference herein. In brief, an enzyme such as alkaline phosphatase is attached directly or is linked subsequently to the oligonucleotide probe. The substrate for the enzyme's catalytic activity is one which provides an intense fluorescent signal and also demonstrates a very large Stoke's shift. Such substrates have been shown to be highly detectable labels when used with conventional in-situ hybridization method. See for example: *Am. J. Human Genet. Suppl.* 55, A271, Abstract #1588(1994); *FASEB J.* 8: A1444, Abstract #1081 (1994); and *Mol. Biol. of the Cell Suppl.* 4,226a, Abstract #1313 (1993).

The user is thus given the option of preparing a nmt55 oligonucleotide probe in several ways. The nucleic acid sequence of the probe may be directly and immediately bound to an identifying dye label (such as those of Table 9) if desired. Alternatively, the nmt55 oligonucleotide probe may be prepared as a molecule having a receiving element such as biotin. The biotinylated probe is allowed to hybridize in-situ; and then a prepared specific binding partner (such as avidin or streptavidin complex) bearing an identifying dye label as a component part can then be added to the reaction fluid after hybridization is completed—thereby causing the identifying label to be joined subsequently as well as indirectly to the immobilized hybridized reaction product. Finally, the interchelators (such as those listed within Table 11), may be used in unmodified form to label double-stranded, hybridized reaction products without any prior intermediate agent. The nmt55 probe in this instance remains unlabeled throughout the entire hybridization process; the interchelators then will bind directly to only the double-stranded reaction product upon reactive contact; and thereby provide an identifying label specific for only the hybridized, double-stranded, reaction product in the diagnostic method.

C. Diagnostic Assay Formats

The technique employing a nmt55 oligonucleotide probe for selective binding to a complementary target sequence is conventionally termed "hybridization". However, the overall development of individual hybridization based assays for the identification of specific nmt55 DNAs, RNAS, and their expression products can be hindered because of difficulties in: (a) isolating highly specific nucleic acid sequences for use as a nmt55 oligonucleotide probe; (b) developing assay formats that are sufficiently sensitive, rapid, and simple in order to identify even one complementary nmt55 oligonucleotide target sequence in a fluid mixture containing many varieties of different single-stranded oligonucleotides in admixture; and (c) devising non-radioactive detection systems that provide a sufficient degree of sensitivity. Thus, several types of DNA and RNA hybridization assay formats can be used.

Four broad types of hybridization assay are conventionally known today which are suitable generally for the diagnostic detection of DNA or RNA coding for nmt55 kDa protein within primary human breast cancer tumor cells. These general hybridization assay formats are: the Southern and Northern blot techniques; the dot or spot blot technique; in-situ hybridization; and sandwich hybridization assays. As with the selection of an appropriate oligonucleotide probe, the choice of a hybridization assay format often rests upon the degree of specificity and sensitivity that is required for the particular analysis; and upon the factors of speed, reliability, and ease of performance and interpretation of the assay result—which varies markedly among the different assay formats.

The Southern and Northern blot assays differ primarily only in the nature of the oligonucleotide target. The Southern technique is designed for DNA analysis while the Northern procedure is intended for RNA analyses. The Southern and Northern blot assays are thus essentially mirror images protocols differing in the details of reagents, concentration and the like. For simply and ease of understanding the Southern blot assay will serve as the illustrative type example.

In Southern blot assays, test specimen DNA from tumor tissue or cells is isolated and purified prior to restriction endonuclease digestion; followed by separation of the digestion products by electrophoresis on an agarose gel, denaturation of the tumor cell DNA in the gel, and transfer of the denatured DNA fragments to a solid matrix such as a nitrocellulose membrane. The tumor cell DNA bound to the solid matrix is then hybridized in the presence of a radioactively labeled nmt55 DNA probe to establish homology between the probe and target DNA. Hybridization of the target DNA to the probes is detected by autoradiography; and this often requires several days or weeks of plate exposure. This format is thus often too lengthy and cumbersome for routine or large-scale analyses of many specimens.

The alternative dot-blot procedure also requires that specimen DNA or RNA from tumor cells be isolated and purified before being denatured and applied to a suitable solid matrix (such as nitrocellulose). Hybridization to the matrix-bound DNA (or RNA) is then performed using a nmt55 probe. The hybridization of target DNA (or RNA) to the probe DNA (or RNA) is detected either by autoradiography or by visual inspection using non-radioactive detection procedures. The spot-blot assay format is similar except that specimens or specimen lysates are directly applied to the solid matrix without prior extraction of their DNA (or RNA). Although this assay format allows many different samples to be processed at one time, these assays are often limited to high background noise that complicates the interpretation of results and is also subject to lengthy time of processing for each sample to be evaluated.

The third format, the in-situ hybridization technique, intends that the DNA or RNA in the tumor cells of a fixed tissue section or fixed culture cell be hybridized to nmt55 DNA (or RNA) probes directly on a microscope slide. The results are determined by microscopy if non-radioactive detection systems are used and by autoradiography if radioisotopes are employed for the targets. A major drawback of this assay format is the inability of the technique to detect the presence of only a few copies of the target DNA (or RNA) sequence to be hybridized. In addition, the conventional in-situ hybridization assay is often cumbersome for screening large numbers of test specimens due to the need to separate and remove extraneous cellular materials from the sample prior to addition of the labeled target.

Lastly, the sandwich hybridization assay requires that at least two different specific nmt55 probes hybridize to the target DNA (or RNA) of interest, rather than just one probe alone. In this format, the first probe (the capture sequence) is bound to a solid support and is allowed to bind (capture) the test specimen DNA (or RNA). A second probe (the signaling probe) with a sequence that is adjacent or close to the capture sequence on the target DNA (or RNA) molecule is then allowed to hybridize to the support-bound target DNA (or RNA). This signaling probe can be labeled with either radioactive or non-radioactive labels; and the removal of non-specific cellular material in the first step of the procedure enhances the specificity of the hybridization assay by reducing the effects of contaminating tissue or debris.

VI. Illustrative Preferred Protocols for Practicing the Invention

It is deemed both useful and desirable to provide some examples of test protocols were be employed by laboratory technicians on-demand to test clinically obtained tumor specimens for metastatic spread. It will be noted and appreciated, however, that the protocols described hereinafter are merely representative and examplary of their kind and type. No limitations or restrictions are to be placed on the user's decision to vary from the stated details of each protocol; rather, the user is free to alter many or all the recited parameters of use to meet his individual needs or personal preferences.

General Preparations:

Isotopes and chemicals $^{35}S$ methionine (protein labeling mix 1175.0 Ci/mmol) and $^{32}Pg$ ATP (3000Ci/mmol) were obtained from New England Nuclear (Boston, Mass). Secondary antibodies (goat anti rabbit IgG and goat anti mouse IgG) and color reagents for western blood analyses were obtained from BioRad. Goat antimouse IgM was purchased from Boehringer Mannheim Biochemicals. Immuno pure goat anti rabbit IgG (H+L) peroxidase conjugate was obtained from Pierce. Dako's quick staining peroxidase kit contained: secondary antibody, streptavidin reagent and the chromogen DAB. Gill's Hematoxylin counterstain was purchased from Shandon, Inc. Oligonucleotides used in the gel shift assays were purchased from Marshal University DNA Core. All pre made gel shift reagents were purchased from Promega.

Clinical Material

Tissue procurement: Human breast cancer tissue is obtained from patients undergoing surgery for treatment of breast cancer. Normal breast tissue specimens are obtained from subjects who undergone breast reconstruction surgery. Patients with primary breast cancer are treated with various therapeutic modalities, at the discretion of their physician. Surgery to remove the primary tumor and analysis of tumor biochemical markers are routine procedures in management of human breast cancer patients.

Human Breast Tissue Specimen Procurement

Human breast tumor biopsies or needle aspiration samples of tumors are procured in the course of treatment of patients with breast cancer. In the operating room, the excised tissue is placed in a container, clearly marked and transported to the pathology department. After pathological evaluation to assess tumor pathological characteristics and to insure that the sample contains tumor cells, a portion of the tumor is placed in a well-marked container and transported to the laboratory on dry ice, where it is stored at −70C until used. In some instances, a needle aspirate biopsy is used to assess tumor presence and characteristics. All steps below apply to the needle biopsy aspirates.

Tissue Handling and Preparation of Cytoplasmic and Nuclear Fractions

The frozen sample is pulverized in a thermovac tissue pulverizer on dry ice and the tissue powder is placed in a clean tube. The tissue powder is homogenized in buffer (Tris-HCI (50 mM), mM sodium ethylene diamie tetraacetic acid (EDTA), 10% glycereol, 10 mM sodium molybdate, 10 mM monothioglycerol, 10 ug/ml aprotinin, 10 ug/ml leupeptin, 0.5 mM phenylmethyl sulphonyl fluoride and 10 ug/ml pepstanin), using polytrone with the appropriate probe depending on the size of the tissue sample. The homogenization is carried out at 0–4C, with 30 second bursts and 1 minute cooling in between bursts. The tissue homogeate is centrifuged at 1000×g for 10 minutes to isolate the nuclear fraction from the cytosolic fraction. The nuclear pellet is washed three times with buffer, by resuspension and recentrifugation.

A First Preferred Protocol Suitable for Detection of nmt55 Protein:

Extraction of nmt55 from Isolated Nuclei

The washed pellet is resuspended in the nuclei-isolation buffer containing 0.4 M KCl. The nuclear suspension is kept in suspension by frequent vortexing. After one hour at 0–4C, the suspension is centrifuged at 100,000×g for 30 minutes to separate the soluble proteins from the nuclear matrix and insoluble chromatin. The supernatant is removed (referred to as nuclear extract) and stored frozen until experimentation.

Gel Electrophoresis:

Resolving gels (10%) are made by mixing 20 ml of acrylamide-bis (30%–0.8% wt/vol), 7.5 ml of 3M Tris-HCI pH 8.8, 31.56 ml of ddH$_2$O and 0.6 ml of 10% SDS, degas for 30 minutes. TEMED (35 μl) is added and the mixture degassed for 30 minutes. Ammonium persulfate (APS) (0.33 ml of 10%) is added and the mixture is immediately poured into gel apparatus using 60 cc syringes. 1-Butanol (1 ml) is overlaid on top of resolving gel, to prevent drying, and the gel allowed to polymerize for 1 hour. The layer of butanol is removed by washing with water, just prior to pouring the stacking gel (see below). The stacking gel consists of 3.75 ml of acrylamide-bis (30%–8% wt/vol), 1.875 ml of 2M Tris-HCI, pH 6.8, 24 ml. of ddH$_2$O, and 0.3 ml of 10% SDS and is allowed to degas for 30 minutes. TEMED (25 μl) is added and the mixture is degassed for 30 minutes. Ammonium persulphate (0.3 ml of 10%) is added and the stacking gel is poured into the gel apparatus with the combs place appropriately. The stacking gel is allowed to polymerize for one hour. The combs are removed and electrode buffer (25 mM. Tris, 192 mM glycine, 4 mM sodium dodecylsulfate, pH approximately 8.3) is added to the gel holder.

Protein samples (with a known concentration) to be resolved are mixed with 5× sample buffer (2 g SDS, 1.0 ml of Triton X100, 3.126 ml of 2M Tris-HCI, 10.8 ml of ddH$_2$O and adjusted to a final volume of 20 ml and pH to 6.8, 100 mg of bromophenol blue, 1.0 ml of mercaptoethanol and 4 ml of glycerol) to give a final concentration of 1× and is layered onto the wells in the gel. A low range molecular weight (MW) markers (BioRad) is included in each gel (10 μl of MW markers to 0.150 ml of 1× sample buffer). The samples are layered onto the gel and electrophased for 12–17 hours at 17mA and 500V, at room temperature.

Electrotransfer of Proteins from the Gel to Nitrocellulose Membranes:

Gels are removed from the apparatus and placed in BioRad trans-blot apparatus, which was filled with transfer buffer (20% methanol, 192 mM glycine and 20 mM Tris, pH 8.3). The gels are transferred to nitrocellulose membrane for three hours at 0–4° C. with stirring, at 0.36A and 100V. Nitrocellulose membranes are either placed between two filter papers and stored at room temperature or used for Western blot analysis immediately.

Western Blot Analysis:

The nonspecific protein binding sites on nitrocellulose membranes are blocked by incubation in buffer TBST/5% fat-free milk (10 mM Tris, 150 mM sodium chloride adjusted pH to 8.0 then added 0.5% Tween 20) for 1 hour on shaker at room temperature (RT). Subsequently, the membranes are washed with TBST and the primary antibodies (in the desired dilutions, 1:1000 or 1:2000 in TBST/5% milk) are added. The antibodies antigen interaction is carried out by gentle shaking at room temperature (RT) for 1 hour. The membranes are then washed 3 times with TBST for 5 minutes each time to remove the unbound primary antibodies. Secondary antibodies (goat-anti-mouse IgG conjugated to alkaline phosphatase for monoclonal and goat-anti-rabbit IgG conjugated with alkaline phosphatase for polyclonal) are added to the membranes at a dilution of 1:2000 and allowed to incubate at RT for 45 minutes with gentle shaking. The membranes are then washed 3 times with TBST for 5 minutes each to remove the unbound secondary antibodies. The bound antibodies are detected by incubation in the appropriate substrate concentrations of alkaline phosphatase. (100 ml of I× AP color development buffer was combined with 1 ml of AP color reagent A (nitroblue tetrazolium in aqueous dimethylformide (DMF), containing magnesium choloride (BioRad) and 1 ml of Ap color reagent B (5-bromo4-chloro-3-indolyl-phosphate in DMF (BioRad). Because the reactants are light sensitive, the membranes must be kept in the dark for 15 minutes with gentle shaking. The membranes are then washed with ddH2O for 10 minutes to stop the reaction. Protein bands are visualized and nitrocellulose membranes dried between two pieces of filter paper.

Detection of Antigens with Enhanced chemilumenscence (ECL):

Detection of antigens in Western blot analysis can be made by a sensitive method using ECL. Horse Radish Peroxidase conjugated secondary antibodies are then used. Subsequent to incubation with the primary antibodies, and washing, immuno pure goat rabbit IgG (H+L) peroxidase conjugated is added to the nitrocellulose membrane (1:50, 000 in TBST/milk). This incubation is carried out at RT for 40 minutes with gentle shaking. The membranes were then washed 4 times for 5 minutes each, with TBST. The membranes are then incubated in one part of stable peroxide solution to one part of luminol/enhancer solution for 3–5 minutes (Pierce), as suggested by the manufacturer. The membranes are wrapped in Saran wrap and placed in a cassette. In a dark room, X-ray film is placed on the membrane for 1–30 seconds. The film is developed and bands visualized.

Detection of nmt55 Antigen in Nuclear Extracts by Dot Blot

Aliquots of breast tumor nuclear extracts are dispensed into a nitrocellulose membrane placed in dot blot apparatus. The protein is allowed to bind for 2–3 hours under gravity, and the membrane washed by TBST buffer. The membrane is blocked with TBST containing 1% bovine serum albumin for 1 h at room temperature, under gravity. The membrane is then washed and the primary antibody against nmt55 is added at the appropriate dilutions (1:1000) and incubated for 4 hours at room temperature. The membrane is then washed with TBST buffer and secondary antibodies conjugated to horse radish peroxidase are added. After 2 h of incubation, the wells are washed with TBST buffer, the membrane removed from the apparatus and incubated in the substrate buffer as described above to visualize the reaction products.

Immunohistochemistry:

Buffers and Solutions:

Phosphate Buffered Saline (PBS): 5 mM Na$_2$PO$_4$, 0.9 mM KH$_2$PO$_4$, 72 mM NaCl, 1.6 mM KCl, ph 7.4.

PBS/Triton X 100: PBS with Triton X 100 at a 1:500 dilution.

Citrate Buffer: 18 ml of 0.1M citric acid and 82 ml of 0.1M sodium citrate.

Five micron sections were cut and mounted onto silane-coated slides. The slides are allowed to dry overnight for best results. Slides are heated at 65C for 45 minutes to 1 hour, and then deparaffinized and rehydrated in xylene three times for 5 minutes each, 100% ethanol two times 3 minutes each and 95% ethanol two times for two minutes. Endogenous peroxidases are blocked by incubating slides in 45 ml of methanol and 5 ml of 30% hydrogen peroxide for 20 minutes. Slides are rinsed with PBS/Triton X-100 two times for two minutes each. Antigen retrieval is performed by adding Citrate Buffer to the glass holder in which the slides are submerged and heated in the microwave for 15 minutes on high; then 5 minutes on 50% power; and then another 5 minutes at 50% power. Slides are then cooled down to room temperature for approximately 30 minutes; and are rinsed in PBS/Triton X-100 two minutes two times. Primary antibody is added at the appropriate dilution to each slide (diluted in PBS, 200 μl on each slide) and incubated for 1 hour at 37C in a humidity chamber. Slides are washed two times for two minutes each with PBS 5% Triton X-100. Biotinylated secondary antibody is applied to the slide for 30 minutes at room temperature. Slides are washed in PBS 5% Triton X-100. Streptavidin is applied for 30 minutes at room temperature in humidity chamber, and slides were rinsed in PBS 5% Triton X-100. Chromogen is added (2.5 ml PBS, ¼ tablet 3,3' diaminobenzidine tetrahydrochloride (DAB) and two drops 0.8% hydrogen peroxide) and incubated for 10 minutes at room temperature in a humidity chamber. Slides are then rinsed in ddH$_2$O for five minutes, counterstained in Gill's Hematoxylin for 1 minute, washed in running water until clear. The cytoplasm is cleared with 0.25% acid alcohol (three dips). Slides are washed under a gentle stream of running water and differentiated in 1% ammonia water for 10 seconds, followed by a wash in running water. Slides are dehydrated by incubating in 95% ethanol 2 times 8–10 dips each; 100% ethanol two times 8–10 dips each; and in xylene three times 10–15 dips each; coversliped with Pemount to be visualized under light microscope. Slides are photographed with Kodak Ectochrome speed 100 film.

A Second Preferred Protocol for Detection of RNA Coding for the nmt55 Protein:

RNA Preparation and Northern Blot Analysis:

Total RNA from human breast tumor tissues is prepared by homogenization in guanidinium isothiocyanate followed by phenol/chloroform extraction and isopropanol precipitation. Total RNA (10–20 μg) is electrophoresed on 1% formaldehyde-3(-N-morpholine) propane sulphonic acid (MOPS) agarose gels and then transferred onto nylon-reinforced nitrocellulose membranes. Membranes are treated with ultraviolet light (Stratalinker, Stratagene; 1200 watt/cm$^2$) to immobilize the nucleic acids.

Double-stranded DNA probes for Northern blot analysis were labeled with α-[$^{32}$P] dCTP using T7 DNA polymerase and random primers. Specific activities range from 10$^8$ to 10$^9$ cpm/μg. Double-stranded DNA probes include a 499 bp Sacl/Bg 1II fragment of human nmt55, and a 545 bp HindIII/Xbal fragment of human glyceraldehyde-3-phosphate dehydrogenase (GAPDH). The probe used for this analysis is desirably a 499 bp Sacl/Bg 1II fragment, representing the unique carboxyl terminus of nmt55. This probe was chosen to avoid possible cross-hybridization with other RNA binding factors such as PSF.

Hybridizations are carried out at 67° C. for two hours in Quickhyb (Strategene). Following low (2×SSC 0.1%SDS, 25° C.) and high stringency (0.2×SSC 0.1%SDS, 65° C.) washes, membranes are exposed to Amersham Hyperfilm for 24–48 h at −70° C. RNA samples are normalized for loading using GAPDH.

The Optional RNase Protection Assay

The RNase Protection Assay system is often an attractive alternative for measurement of RNA. RNase protection assays are preferably carried out using Ambion's commercially available RNase protection assay kit (RPAII). Antisense probes from pGEM3zf(-) nmt55 (499 bp) Sacl/Bg 1II fragment of human NMT-55 subcloned into Sacl/BamHI pGEM3zf(-) are prepared by transcribing Sacl digested plasmid with SP6 RNA/polymerase. Hybridization is carried out for 18 h at 45° C. The hybridization products are digested with RNaseA/T1 for 90 minutes at 37° C. After inactivation of RNase and precipitation of the protected fragments, samples are dissolved and analyzed by gel electrophoresis on 5% polyacrylamide/8 M urea denaturing gels (40 cm). The gels are dried, and subjected to autoradiolgraphy. RNA Century Markers (Ambion) are radiolabeled according to the manufacturer's instructions and used as molecular weight markers.

A Third Preferred Protocol for Detection of DNA Coding for nmt55 Protein:

The isolation and extraction of DNA from tumor cells is performed as previously described herein.

Southern blot analysis of DNA

Human tumor cell DNA (20μg is digested with restriction endonucleases (EcoRI, Hind III, Ncol and Pstl; genomic grade, high concentration), and electrophoresed on 1% agarose gels as previously described. The gels are transferred onto nylon-reinforced nitrocellulose membranes, and treated with ultraviolet light (Stratalinker, Stratagene; 1200 watt/cm$^2$) to immobilize the nucleic acids. Double-stranded DNA probes for Southern blot analysis are prepared as described in the experiments for Northern blot analysis (above), using a 499 bp Sac/Bg 1II fragment of human nmt55. Hybridizations are carried out at 67° C. for two hours. Following low (2×SSC 0.1%SDS, 25° C.) and high stringency washes (0.2×SSC 0.1%SDS, 65° C.), membranes are exposed to Hyperfilm for 24–48 h at −70° C.

VII. Experimental and Empirical Data

A series of experiments and resulting data are provided below which demonstrate and reveal the capabilities, attributes, characteristics, and functional value of the present invention. While the provided experiments and resulting data relate to specific test circumstances and conditions, it will be recognized and appreciated that neither the experimental design nor the empirical data presented therefore limit or restrict the present invention in any substantive manner whatsoever. To the contrary, the experiments and data presented are merely representative and illustrative of the intended applications and use circumstances under which the invention may be diagnostically used advantageously and beneficially.

Experiment 1

Detection of the nmt55 Protein in Human Breast Cancer Cells

SDS-Polyacrylamide Gel Electrophoresis (SDS/PAGE) and Western Blot analysis

Polyacrylamide gel electrophoresis and Western blot analyses were carried out as described previously [Traish et al., *Steroids* 59: 362–370 (1994)]. Briefly, cytosols and nuclear KCl extracts were prepared in the appropriate buffers, as described [Traish et al., *Diag. Mol. Pathol.* 4: 220–228 (1995); Traish et al., *Steroids* 59: 362–370 (1994); and Traish et al., *Endocrinology* 118: 1327–1333 (1986)]; and electrophoresed on 10% SDS/PAGE according to the method of Laemmli [*Nature* 227: 680–685 (1970)]. The proteins were electrotransferred onto nitrocellulose membranes. Strips of the nitrocellulose membranes were then incubated in buffer TBST (50 mM Tris-HCl, pH 8.0, 0.15 M NaCl, 0.5% Tween 20) containing 5% non-fat dry milk to block nonspecific binding sites for 1 h at 37° C.; and then probed for 2 h at 30° C. with the appropriate dilution of the Mab NMT-1 antibody in the same buffer containing 5% non-fat milk. The results are illustrated by FIG. 4.

Figure 4:
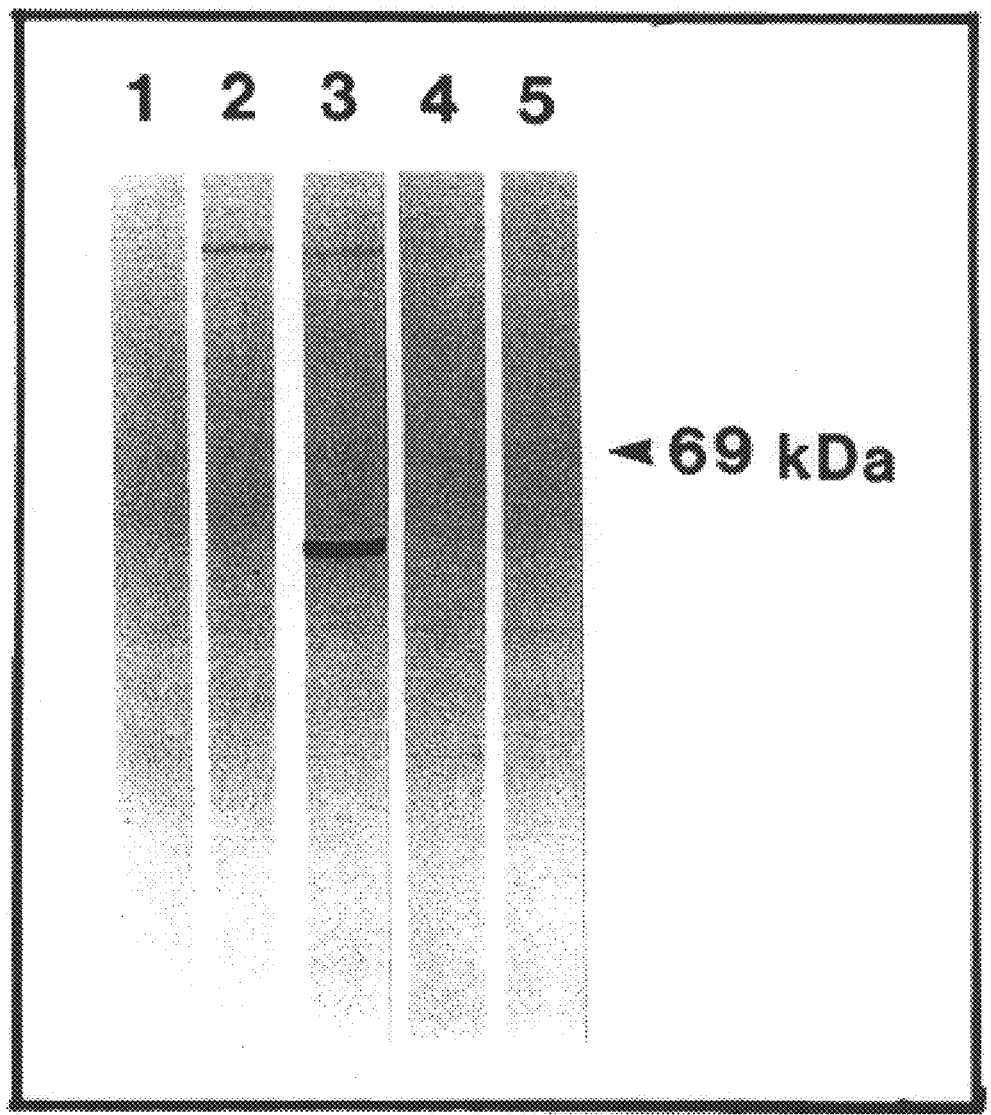
FIG. 4 is a photograph of a Western blot analysis of nuclear and cytosolic extracts from MCF-7 cells using NMT-1 monoclonal antibody.

As seen in FIG. 4, nuclear KCl-extracts Lane (lanes 1, 2, 3 and 5) and cytosol (lane 4) were analyzed by sodium dodecyl suphate polyacrylamide gel electrophoresis (SDS/PAGE), transferred onto nitrocellulose membranes, and subjected to immunoblotting. The arrow represents the migration of bovine serum albumin (BSA, 69 kDa). Lane 1 was immunoblotted with pre-immunserum; Lane 2 represents immunoabsorption of the antibody with the synthetic immunogenic peptide; Lanes 3 and 4 were immunoblotted with Mab NMT-1 antibody; Lane 5 was immunoblotted with antibodies against RARα.

Identification and Characterization of a 55 kDa Nuclear Protein in Human Breast Cancer The monoclonal antibody (Mab NMT-1) as described previously herein was raised to a unique peptide from the human ER did not recognize denatured ER on Western blots but did react with a 55 kDa non-receptor protein solubilized by extraction of nuclei from human MCF-7 cells with buffer containing 0.4 M KCl. This is shown by FIG. 4, lane 3. The 55 kDa protein band was not detected by pre-immune serum (FIG. 4, lane 1) or with antibodies to retinoic receptor (RARα) (26) (FIG. 4, lane 5), progesterone receptor or with monoclonal antibodies directed to other various regions of ER (data not shown). This shows that Mab NMT-1 recognizes an epitope on this 55 kDa protein. Preincubation of the monoclonal antibody with the segment constituting amino acid nos. 140–154 of human ER effectively inhibited the binding of the NMT-1 antibody to this protein segment, as shown by the absence of any immunoreactivity (FIG. 4, lane 2). This 55 kDa protein was detected only in nuclear KCl-extracts but not in low salt cytosolic extracts (FIG. 4, lane 4) showing that this protein is tightly bound to nuclear components. The inability of the monoclonal antibody NMT-1 to detect ER after SDS/PAGE fractionation was confirmed by using ER specific antibodies which detect ER in the same blots (data not shown). This data reveals that the Mab NMT-1 which detects nmt55 protein nevertheless failed to detect ER on Western blot analyses because its epitope on ER, once denatured by SDS, could not be renatured under these Western blot test conditions.

Figure 5:
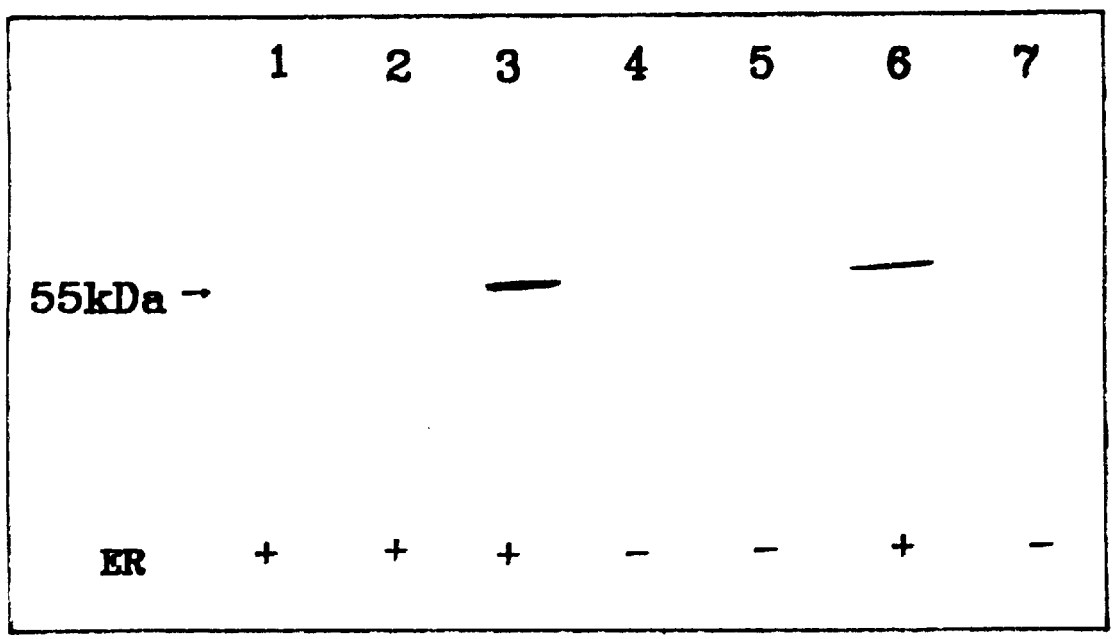
FIG. 5 is a photograph of a Western blot analysis of nuclear extracts from multiple ER+ and ER− human breast tumors showing the presence and absence of the nmt55 kDa protein in individual specimens.

Western Blot Analysis of nmt55 Protein in Nuclear KCl-extracts of Human Breast Tumors Nuclear KCl-extracts from ER+ and ER− human breast tumors were prepared and analyzed by Western blot using Mab NMT-1 antibody. The results are given in FIG. 5. Presence or absence of ER in these tumors is indicated at the bottom of FIG. 5.

Experiment 2

Distribution of the nmt55 Protein Among Animal Species and Cell Types

To investigate if nmt55 protein is conserved among various animal species and to determine what its distribution among the various tissues and cells might be, nuclear extracts derived from a range of different, medically normal tissues and cells by Western blots were tested and analyzed.

Tissues and Cells

Rat uterine tissue was obtained from mature female animals. Mice uterine tissue were obtained from mature mice. The uteri were stripped of fat and mesenteric tissue and kept frozen at −80° C. until use. Calf uterine tissues were obtained from a local slaughter house, placed on dry ice, and transported to the laboratory. Rat kidney, bladder, spleen, brain, testis, liver and prostate were obtained from mature male animals. B16 melanoma cells were a gift from Dr. Richard Niles (Marshall University WV). CHO cells were obtained from Dr. M. Brann (University of Vermont). Human breast cancer tissues were obtained from patients undergoing surgery for breast cancer. Tissues were placed on dry ice and transported to the laboratory where it is stored at −80° C. until experimentation. Nuclear KCl-extracts from several tissues and cells were electrophoresed, electrotransferred onto nitrocellulose, and immunoblotted with MAb NMT-1. The results are shown in FIG. 6.

Animal Distribution

Figure 6:
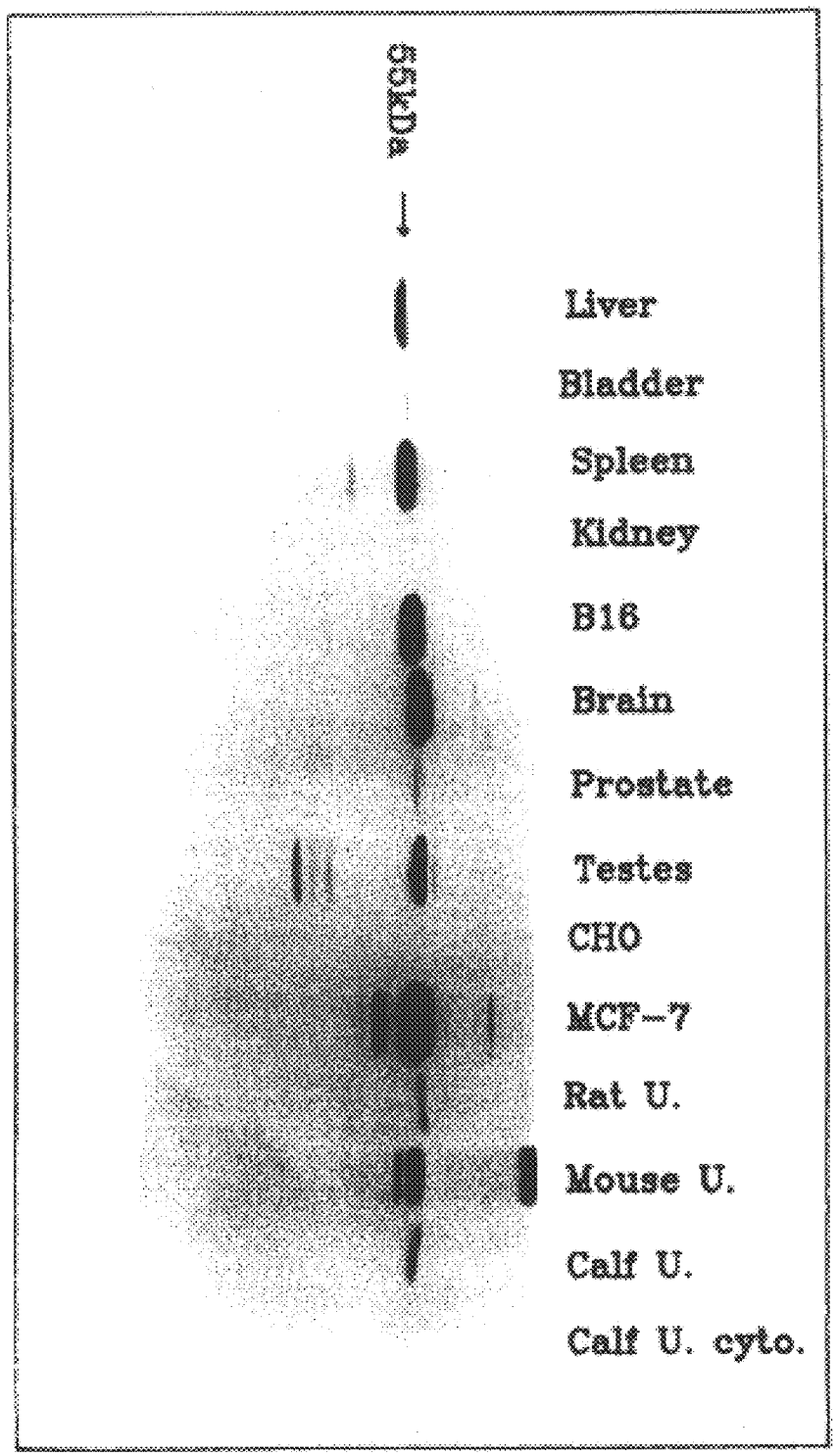
FIG. 6 is a photograph of a Western blot analysis showing the distribution of nmt55 kDa protein in normal tissues and cells.

As shown in FIG. 6, nmt55 protein was detected in nuclear extracts of cells from porcine brain, rat liver, spleen, testes, and uterus. This nmt55 protein was also present in nuclear extracts from MCF-7 cells and B16 melanoma cells. In addition, this protein was detectable in prostate, kidney, and bladder tissues, albeit at a lower concentration; but was not detectable in CHO cells.

Figure 7A:
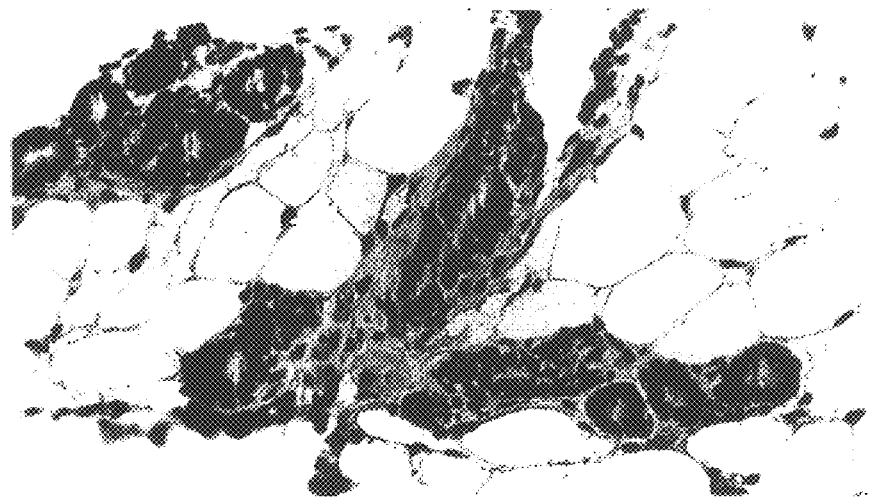
FIGS. 7A and 7B are photographs showing immunohistochemical analyses of normal rat mammary gland showing the presence of nmt55 protein.
Figure 7B:
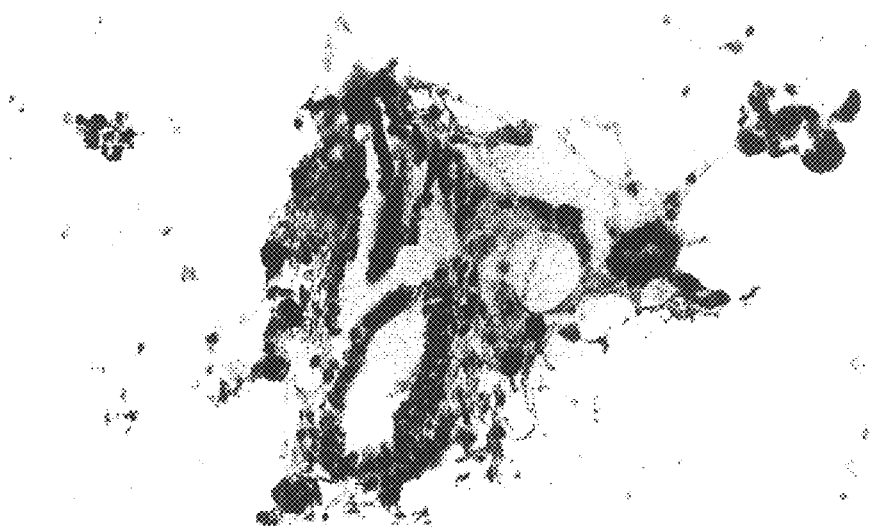

Also, immunohistochemical analysis of normal rat mammary gland as illustrated by FIGS. 7A and 7B showed positive staining within the epithelial and stroma, showing that this nmt55 protein is expressed routinely in normal mammary gland cells. These data and observations reveal that this nmt55 protein is conserved among animal species and its presence in many normal tissues and cell types indicates its important biological function.

Expression of nmt55 in Normal Human Breast Tissue

Figure 8:
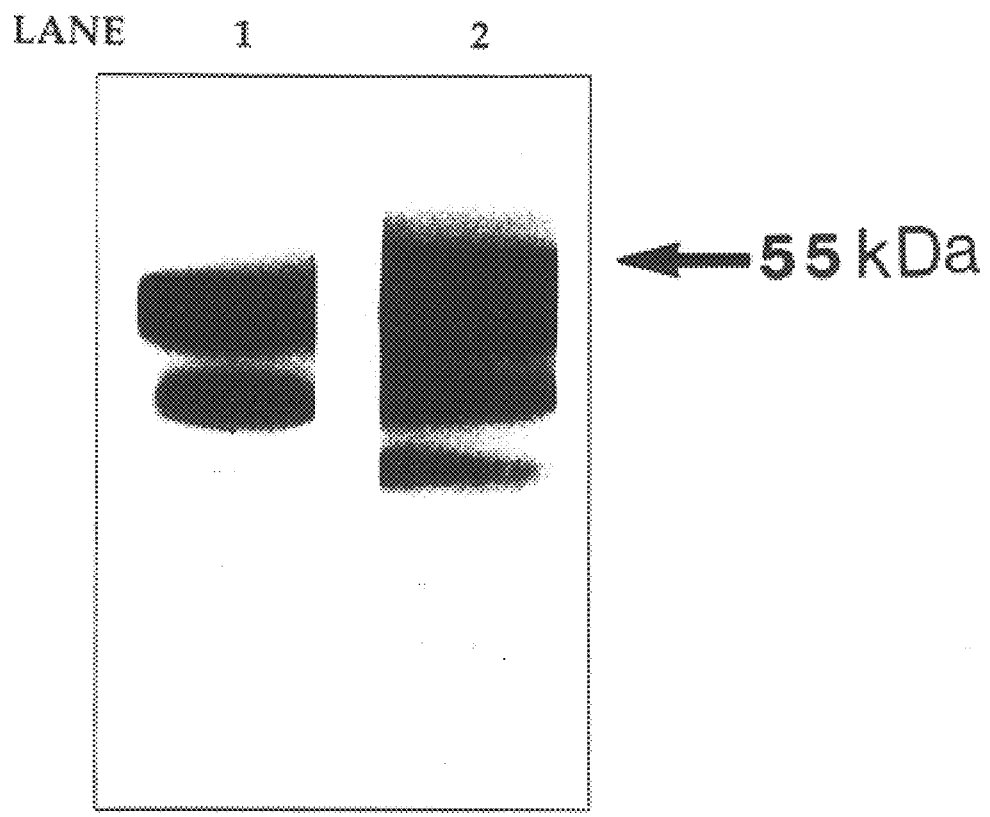
FIG. 8 is a photograph of a Western blot analysis showing the presence of nmt55 protein in normal human breast tissue.

Furthermore, the nmt55 protein is expressed in normal human breast tissue and cells. Normal human breast tissue was procured from subjects undergoing breast reconstruction surgery. Nuclear and cytosolic fractions were prepared and analyzed for the expression of nmt55 protein by Western blot analysis. As shown in FIG. 8, nmt55 is expressed in normal human breast tissues (lane 2 represents 150 ul of nuclear extract and lane 1 represents 75 ul of nuclear extract. The data reveals and demonstrates the presence of nmt55 protein in normal breast tissues and cells within human subjects.

Experiment 3

The nmt55 Genomic DNA

A proper understanding of the role for this nmt55 protein in breast cell growth and function is provided by some detailed studies to show its biological and biochemical function. As a first step towards this goal, the characterization of the nmt55 gene in human breast cancer cells was performed.

Preparation of Genomic DNA

Human placental genomic DNA (20 μg) was digested with a variety of restriction endonucleases (EcoRI, Hind II, Ncol and Pstl; genomic grade, high concentration), and electrophoresed on 1% agarose gels. The gels are transferred onto nylon-reinforced nitrocellulose membranes, and treated with ultraviolet light (Stratelinker, Stratagene; 1200 watt/$cm^2$) to immobilize the nucleic acids. Double-stranded DNA probes for Southern blot analysis are prepared as described in the experiments for Northern blot analysis below, using a 499 bp Sac/Bg 1II fragment of human nmt55. Hybridizations are carried out at 67° C. for two hours. Following low (2×SSC 0.1%SDS, 25° C. and high stringency washes (0.2×SSC 0.1%SDS, 65° C.), membranes are exposed to Hyperfilm for 24–48 h at −70° C.

Southern Blot Analysis of nmt55 Genomic DNA

Figure 9:
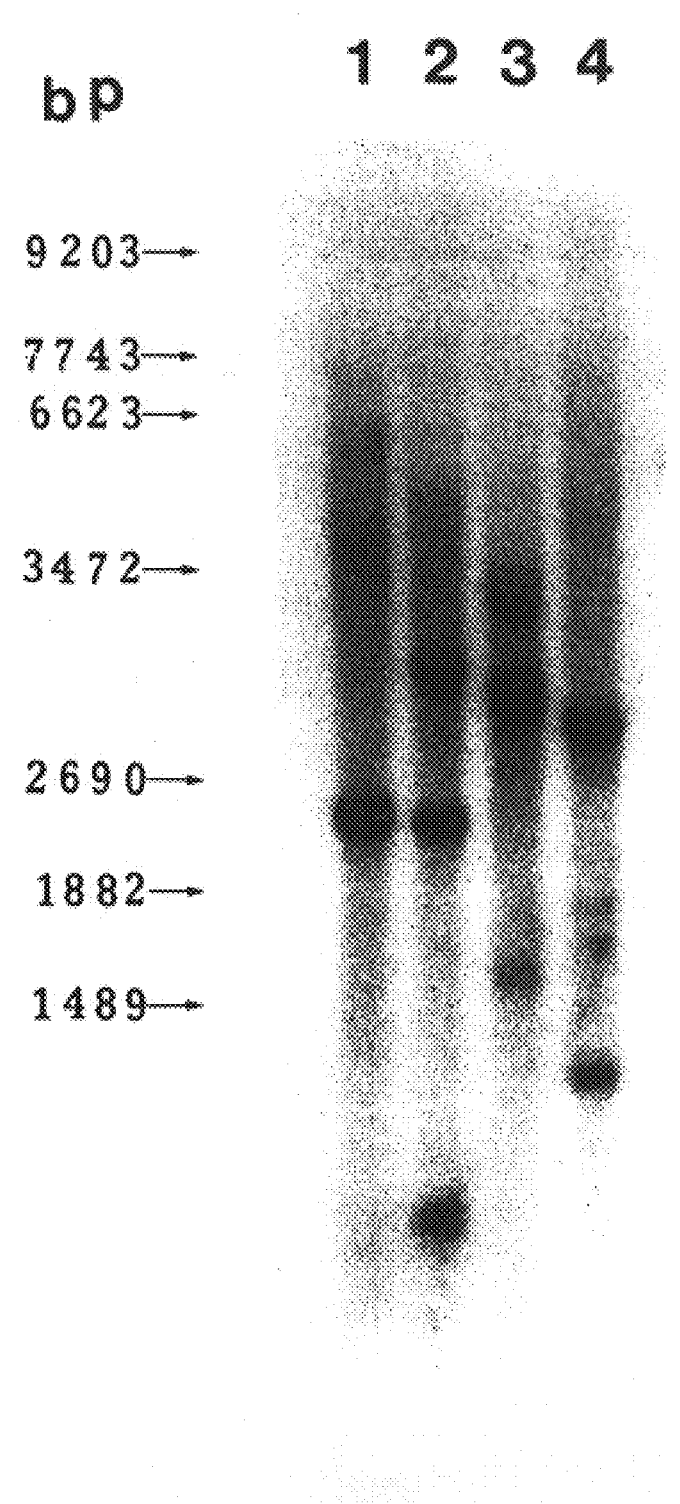

FIG. 9 shows the result of genomic DNA isolated from human placenta; digested with EcoRI (lane 1), HindIII (lane 2) Pstl (lane 3) and Ncol (lane 4); and electrophoresed on 1% agarose gels. The DNA was transferred onto nylon-reinforced nitrocellulose and hybridized with the radiolabeled probe (a 449 bp Sacl/Bg 1II cDNA fragment). Subsequent to high stringency washes the blot was dried and exposed to X-ray film. The size of the radiolabeled bands was determined by molecular weight markers. (Lambda DNA digested with StyI).

As revealed by FIG. 9, the product of EcoRI digestion hybridized to a single 2.3 kb band shows the presence of a single copy of this gene. DNA digested with HindIII showed three bands (3.5, 2.3 and 0.7 kb) despite the presence of a single HindIII site in the cDNA approximately 330 bp 3' to the probe. This shows the presence of one or more intervening sequences in this region. This observation is supported by the hybridization products subsequent to digestion with PstI (~4.4., 3.2 and 1.4 kb), since PstI site is absent in the cDNA. Digestion with NcoI resulted in hybridization to a 2.9 and 1.1 kb bands. Since the two NcoI sites predicted from the cDNA sequence flank the probe and would be expected to yield only a 0.96 kb fragment, the hybridization pattern obtained reveals that the 2.9 and 1.1 kb bands is the result of intervening sequences.

Experiment 4

RNA Coding for nmt55 Protein

RNA Preparation and Northern Blot Analysis

Total RNA from MCF-7 cells and human breast tumor tissues was prepared by homogenization in guanidinium isothiocyanate followed by phenol/chloroform extraction and isopropanol precipitation [as described in Chomczynski, P. and N. Sacchii, *Anal. Biochem.* 162: 156–159 (1987)]. Total RNA (10–20 μg) was electrophoresed on 1% formaldehyde-MOPS agarose gels and then transferred onto nylon-reinforced nitrocellulose membranes. Membranes are treated with ultraviolet light (Stratalinker, Stratagene; 1200 watt/cm$^2$) to immobilize the nucleic acids. Double-stranded DNA probes for Northern blot analysis were labeled with α-[$^{32}$P] dCTP using 17 DNA polymerase and random primers. Specific activities range from 10$^8$ to 10$^9$ cpm/μg. Double-stranded DNA probes include a 499 bp SacI/BgIII fragment of human nmt55, and a 545 bp HindIII/XbaI fragment of human glyceraldehyde-3-phosphate dehydrogenase (GAPDH) [as described in Tso et al., *Nucleic Acid Res.* 13: 2485–2582 (1995)]. The probe used for this analysis was a 499 by SacI/BG 1II fragment, representing the unique carboxyl terminus of nmt55. This probe was chosen to avoid possible cross-hybridization with other RNA binding factors such as PSF. Hybridizations were carried out at 67° C. for two hours in Quickhyb (Strategene). Following low (2×SSC 1.0%SDS, 25° C.) and high stringency (0.2×SSC 0.1%SDS, 65° C.) washes, membranes were exposed to Amersham Hyperfilm for 24–48 h at −70° C. RNA samples were normalized for loading using GAPDH. The results are shown in FIG. 10.

Characterization of nmt55 mRNA Expression by Northern Blot Analysis

Figure 10:
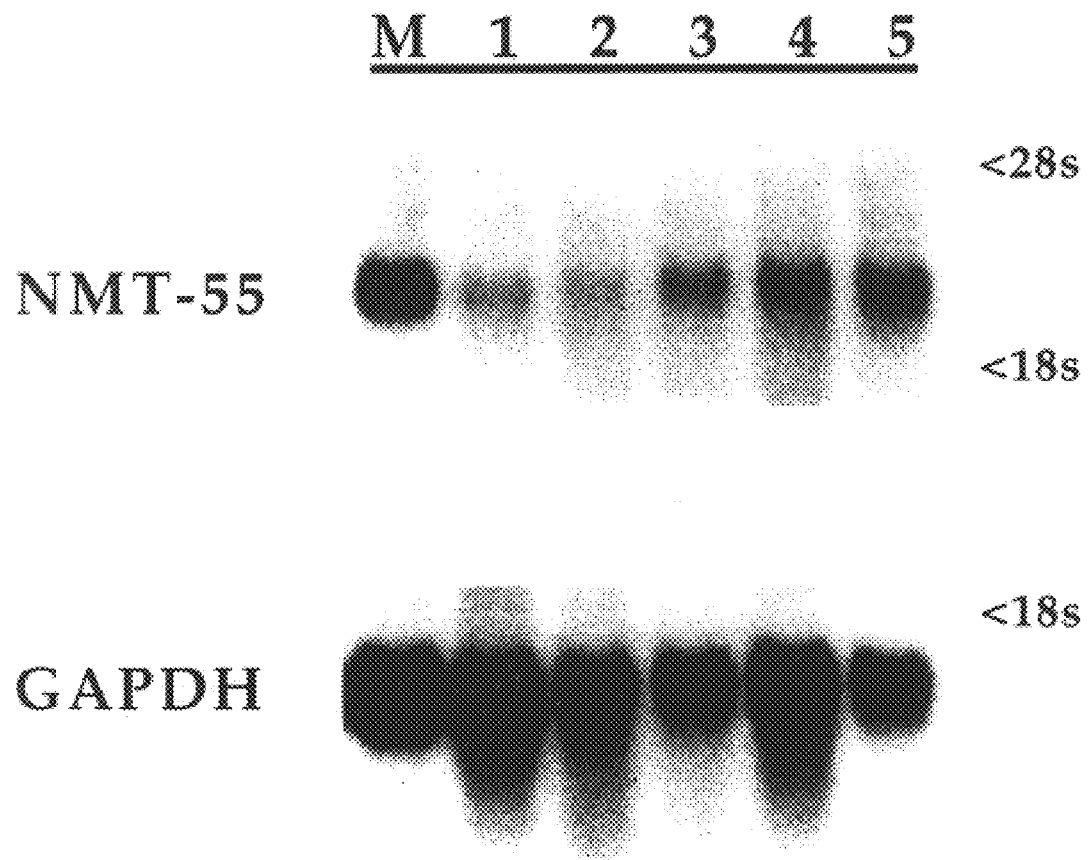
FIG. 10 is a photograph of a Northern blot analysis of nmt55 mRNA extracted from MCF-7 cells and human breast tumor cells.

FIG. 10 (lane M) shows that MCF-7 cells express a relatively abundant 2.6 kb mRNA transcript for nmt55. Analysis of total RNA from five ER+/PR+ human breast tumors (FIG. 10, lanes 1–5) demonstrated different levels of nmt55 mRNA expression. The low levels of expression observed in tumors represented by lanes 1 and 2 are not due to different RNA loading, since GAPDH mRNA levels were similar for all tumor samples. In earlier preliminary experiments, tumors which were ER− and PR− did not express detectable nmt55 transcripts (data not shown). The tumors used in these preliminary experiments also expressed different levels of nmt55 protein, as determined by Western blot analysis (data not shown).

The RNase Protection Assay

Figure 11:
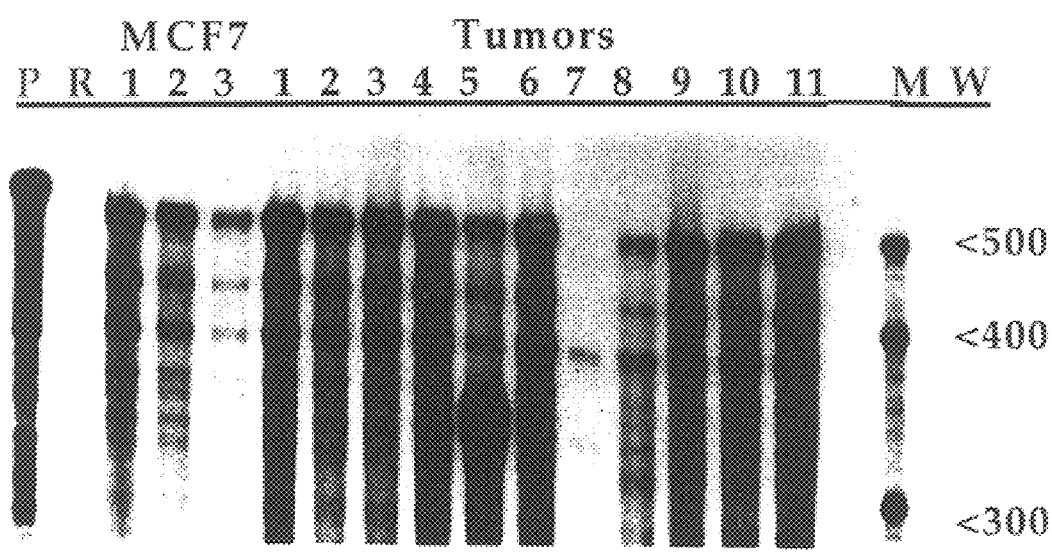
FIG. 11 is a photograph of an RNase Protection Assay showing the RNA extracted from primary human breast tumors and the MCF-7 human breast cancer cell line.

Analysis of RNA extracted from human breast cancer cell line MCF-7 cells and from primary human breast tumors by RNase protection assay is shown in FIG. 11. Lane P represents the radiolabeled probe used. Lane R is the antisense probe digested with RNase. Note there is no band in this line, indicating complete digestion. Lanes marked 1, 2 and 3 represent decreasing concentrations of RNA from MCF-7 cells. Note that there is a band with approximate size of 499 bp representing the protected fragment. Lanes 1–6 and 8–11 represent RNA extracted from primary human breast tumors. Lane 7 represents RNA extracted from calf uterine tissue. Lane marked M represents the Molecular Weight markers. Note that human breast tumors express varying degrees of RNA for nmt55. This assay is specific for human RNA since as shown in lane 7, calf RNA is completely digested as indicated by the absence of a band at the 499 bp. These results clearly suggest that this assay is a very sensitive assay for detecting RNA in human primary tumors.

Experiment 5 cDNA, RNA and nmt55 Protein Analysis

To determine the genomic content and expression of nmt55 protein, cDNA cloning techniques were utilized; and the corresponding RNA and amino acid sequence for the nmt55 kDa protein were deduced. The procedures are described below.

Bacterial Strains

*Escherichia coli* strain XL1 Blue (genotype F'::Tn10proABlacl$^q$ Δ (lacZ)/recA1 endA1 gyrA96 (Nal$^r$) thi-hsdR17 (r$_k$-m$_k$+) supE44 relA1 lac (Stratagene) was used for all lambda phage experiments and DH5α (genotype F'endA1 recA1 relA1 hdsR17 (r$_k$-m$_k$+), supE44 gyrA (Nal$^r$) thi-1,Δ (laclZYA-argF) U169 deoR (φ80 dlac Δ (lacZ)M15); (Life Sciences Inc.) was used in the transfection and preparation of plasmid DNAs.

Library Screening and Subcloning

A lambda ZAP II (Strategene) cDNA library of MCG-7 cells (complexity-1×10$^7$) was screened using expression cloning with IPTG-induction and Mab NMT-1. Recombinant phage were plated at a density of ~50,000 pfu per 150 mm Petri dish. Plaque lifts were prepared and probed (135 mm nitrocellulouse, Scheicher and Scheull). In order to avoid selecting ER clones, the nitrocellulose membranes were soaked in 0.1% SDS in Westernblot buffer, and then washed with buffer containing 10% methanol. This treatment denatures ER protein and does not permit detection of ER on Westernblots by NMT-1. Positive plaques were isolated and purified to homogeneity. pBluescript plasmids corresponding to the positive phage were excised, according to manufacturer's instructions. To determine insert sizes, polymerase chain reaction (PCR), using T3 and T7 RNA polymerase promoter primers (Strategene) was carried out. The primers used flank the cloned sequences in pBluescript. PCR followed by agarose gel electrophoresis revealed two clones with approximate sizes of 2.5 kb and 1.7 kb for the inserts. Restriction analysis with XhoI and EcoRI (the sites for insertion of cDNA into lambda ZAPII) revealed a complex pattern indicating either internal EcoRI and/or XhoI restriction sites. Induction of bacteria harboring the plasmid (pbluescript nmt55) with 2 mM IPTG for 5 hours followed by isolation and lysis of the bacteria SDS sample buffer, SDS-PAGE, and Western blotting resulted in an immunoreactive ~60 kDA band, in agreement with a predicted 55 kDa protein. The 1.7 kb clone yielded a smaller protein product indicative of an internal methionine start site (data not shown).

Expression of nmt55 in Bacteria

Cultures of DH5α harboring the appropriate plasmids were grown to late log phase (A600~1A). Bacteria harboring the 2.5 kb cDNA clone did not grow when induced with isopropylthiogalactose (IPTG), suggesting a detrimental effect of the gene product in bacteria. To overcome this, cells were grown for three hours prior to induction with IPTG, and then induced with 200 mM IPTA with shaking at 300 rpm 37° C. for 5 hours. Aliquots of bacteria cultures were centrifuged in 1.5 ml microfuge tubes and the cell pellets lysed by boiling in 1X SDS-PAGE sample buffer. After 5 minutes of centrifugation to remove cell debris, aliquots of the supernatants were electrophoresed on 10% SDA-PAGE, electrotransferred and processed for Western blot analysis.

Nucleotide Sequencing of cDNA Clones

Plasmids were prepared from candidate bacteriophage clones by co-transfection of XL-1 Blue with the helper M13 phage R408 (Stratagene) and the lambda phage. The resulting phagemids were transfected into DH5α, positive clones selected on ampicillin containing plates, screened, and plasmids were prepared. The insert DNA was sequenced in both directions using primers every 300 base pairs at the Boston University DNA Core Facility, using an Applied Biosystems International (ABI) 3000 DNA sequencer.

B. Results

Cloning of nmt55 DNA from MCF-7 cDNA Library

Two cDNA clones from MCF-7 cells were isolated and sequenced; one represented a full length 2.5 kb clone and a 1.7 kb clone which was an internal fragment of the 2.5 kb. The 2.5 kb cDNA encompassed 115 bp 5' untranslated, a 1416 bp open reading frame, and ~970 bp of 3' untranslated sequence terminating at poly A. This is shown by FIG. 12. The open reading frame was predicted to encode a 471 amino acid protein (54,197 Da), in good agreement with the observed 55 kDa apparent molecular weight determined by Western blots from nuclear KCl extracts. No unique sequences were identified with homology to ER, expect 5 amino acids (Ala Ala Pro Gly Ala) which were found in the C-terminal region of nmt55 protein and represent the epitope of NMT-1 (see below).

Amino Acid Sequences, Location of the RNA Binding Domains and Binding Epitopes

The amino acid sequence of nmt55, deduced from the cDNA, is also shown in FIG. 12. Several interesting features are noted: a glutamine and histidine rich regions (Q/H) located in the amino terminus (residues 19–35); a predicted bipartite RNA domain (RBD), residues 75–147 and 149–228; a putative helix-turn helix motif (HTH), residues 287–335; and a region rich in acidic (glutamic) and basic (arginine) residues (A/B) extending from residue 318 to residue 368. These structural features, together with its nuclear locationzation, demonstrate that this protein plays a role as a nucleic acid binding protein.

When the open reading frame was screened against the GenBank database, two clones of high homology were found, one murine [Yang et al., *Mol. Cell Biol.* 13: 5593–5683 (1993)] and one human [Dong et al., *Nucleic Acids Res.* 21: 4085–4092 (1993)]. One of these clones isolated from HeLa cells has a high homology to PSF family of RNA splicing factors and contains a bipartite RNA binding motif. The murine candidate had high homology to the OCT-2 family of transcription factors as well as RNA binding motifs. As shown in FIG. 13, the RNA recognition motifs of nmt55 share considerable homologies with those of HeLa p54$^{nrb}$, PSF, NonO and NonA/BJ6. Also, nmt55 protein has a homologous region in the predicted helix turn helix motif with HeLa p54$^{nrb}$, and NonO. This is shown by FIG. 14.

Experiment 6

New Polyclonal Antisera

Using the amino acid sequence of FIG. 1, new polyclonal antibodies were developed to nmt55. Antisera (NMT-4) was raised to a peptide in the N-terminal region which encompasses amino acids 56–72 of nmt55; and other antisera (NMT-5) was raised to a peptide in the carboxyl terminal region spanning amino acids 371–386 of nmt55. These peptides were chosen as immunogens because they have no homology with other proteins; and thus the generated antibodies will avoid cross-reactivity with other RNA binding proteins which share some homology with nmt55 (e.g. PSF).

Specific, Site-directed, Polyclonal Antibodies

Four different polyclonal antibodies were generated for specific regions of the nmt55 protein. The antibodies made against the carboxyl terminus peptide are referred to as NMT5A and 5B, while the antibodies raised against the amino terminus peptide are designated NMT4 A and B. The designation of A and B represent two different host animals that were used to produce the polyclonal antibodies.

Figure 15:
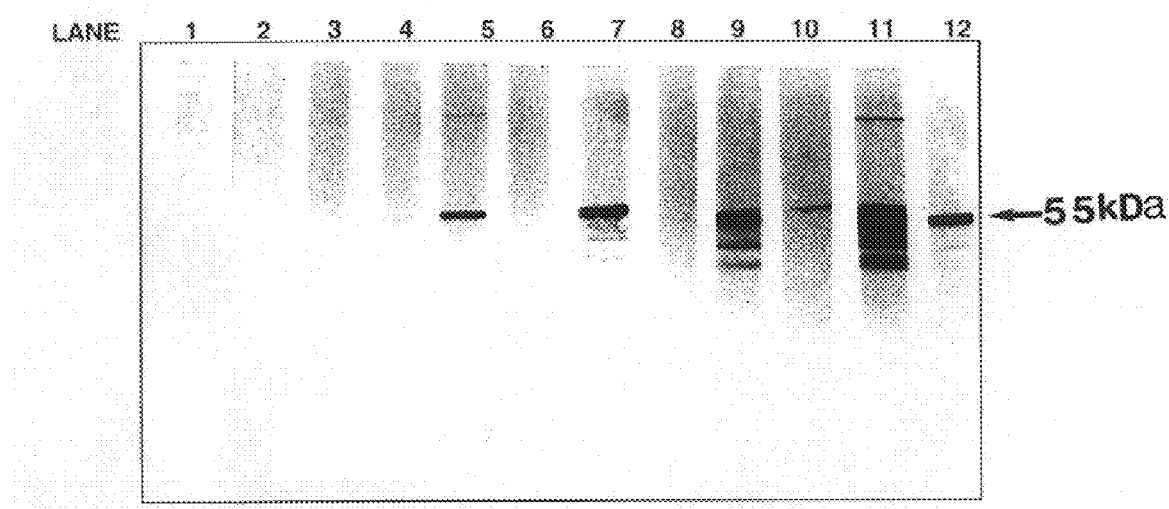
FIG. 15 is a photograph illustrating the interaction of specific polyclonal antibodies with nmt55 protein.
Figures 16A, 16B:
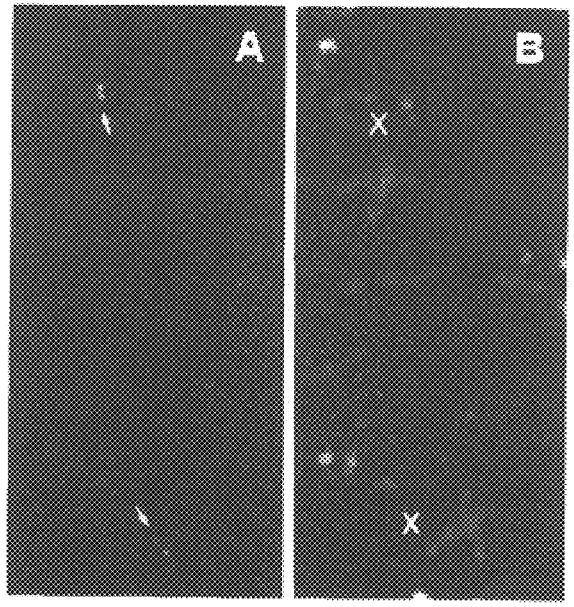
FIGS. 16A and 16B are photographs showing FISH chromosomal mapping of the nmt55 gene on human chromosome X.
Figure 17:
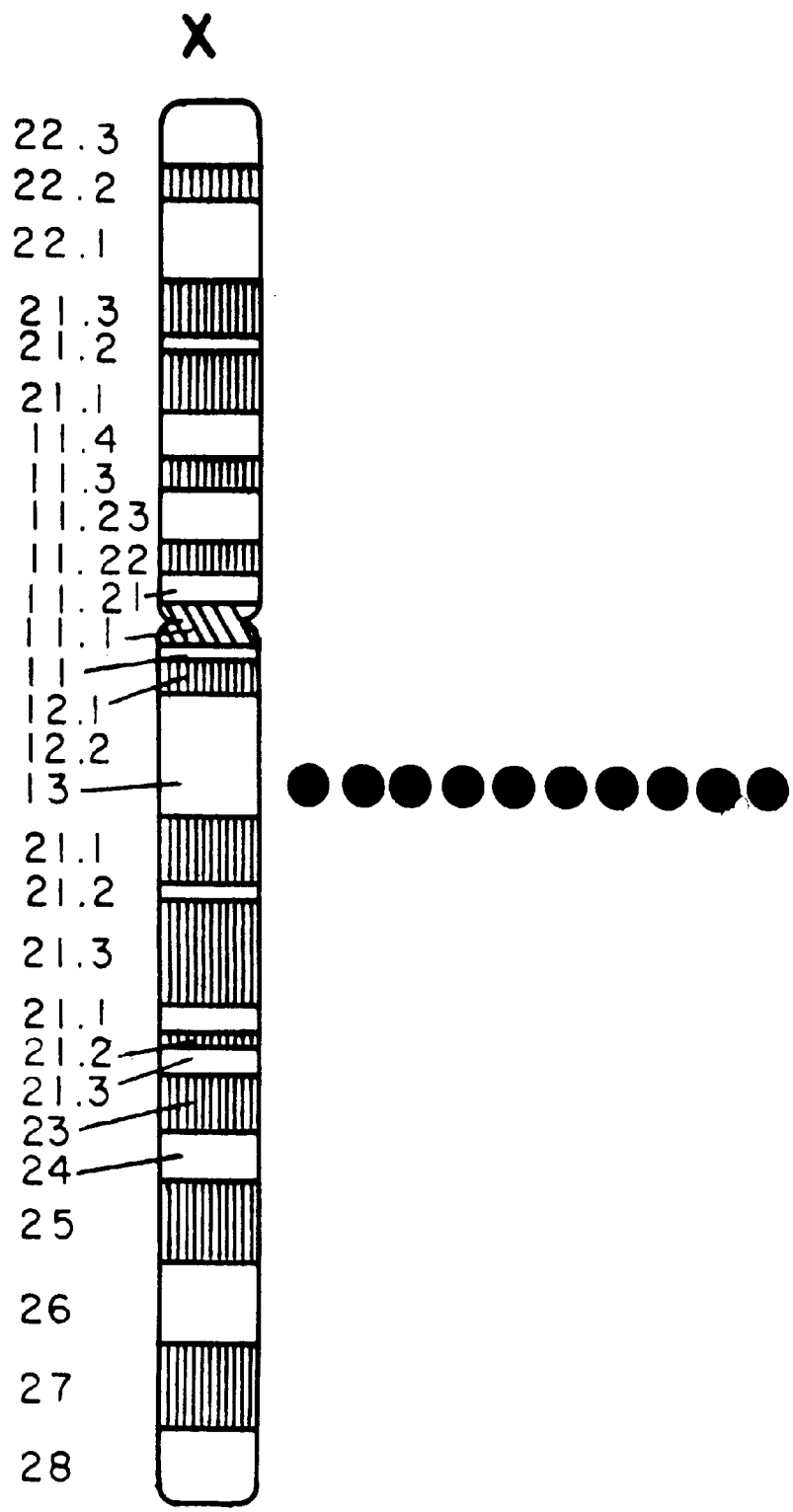
FIG. 17 is a diagram of the FISH chromosomal location of the nmt55 gene on human chromosome X.

FIG. 15 shows the interaction of the newly developed polyclonal antibodies with nmt55 protein. MCF-7 nuclear extract (100 µg) was layered onto a 10% SDS-PAGE and electrophoresed overnight at 17mA and 500V. The resolved proteins were electrotransferred to nitrocellulose membranes for 3 hours at 0–4° C. at 0.36A/100V. Nitrocellulose membranes were cut into strips and probed with different antibodies. Lane 1 represents pre-immune serum from animals immunized with oligopeptide to NMT5A. Lane 2 represents NMT5B pre-immune serum. Lane 3 represents NMT4 pre-immune serum. Lane 4 represents NMT4B pre-immune. Lane 5 shows the nuclear extract probed with NMT5A antibody and lane 6 represents the same antibody pre-incubated with the immunogenic free peptide (NMT5). Lane 7 represents NMT5B and lane 8 represents NMT5 with the antigenic free peptide. Lane 9 represents NMT4A antibody and lane 10 represents NMT4A with the free antigenic peptide. Lane 11 represents NMT4B and lane 12 represents NMT4B with the free peptide. These data show that the pre-immune sera (lanes 1–4) do not detect nmt55 protein, but anti-peptide antibodies raised against nmt55 interact with nmt55 as shown by the appearance of a specific band at approximately 55 kDa (lanes 5, 7, 9 and 11). This molecular mass of the migrating protein is in good agreement with the predicted MW for nmt55. The antigenic peptides competed for the binding of the antibodies (lanes 6, 8, 10 and 12). These observations demonstrate that these antibodies are very specific for nmt55. The displacement in lane 12 was not complete as shown by reduced intensity of the band, which may be due to the high titer of the antibody and greater affinity of the antibody to nmt55 compared to the free peptide.

Experiment 7

Chromosomal Mapping

Fluorescent In-site Hybridization (FISH)

Biotinylation of the cDNA probe (2.5 kb) with DATP using BRL BioNick labeling kit (15° C., 1 h) was carried out as described [Heng et al., *Proc. Sec. Natl. Acad. Sci.* 89: 9509–9513 (1992)]. In-situ hybridization was performed by the FISH method as described by Heng et al. [*Chromosoma* 102: 325–332 (1993)]. Slides were baked at 55° C. for 1 h and after RNase treatment, DNA on the slides was denatured 70% formamide in 2×SSC for 2 minutes at 70° C. and dehydrated by ethanol. Probes were denatured at 75° C. for 5 minutes in a hybridization mix consisting of 50% formamide and 10% dextran sulphate. Probes were loaded onto the denatured chromosomes on slides. After overnight hybridization, slides were washed and the signal was detected and amplified. FISH signals and DAPI banding patterns were recorded separately, in the same field, by fluorescent photomicroscopy, using appropriate filters. The assignment of FISH mapping data with chromosomal bands was achieved by superimposing FISH signals with DAPI banded chromosomes [Methods in Molecular Biology: In-situ Hybridization Protocols, Humana Press, 1994, pp. 35–49].

Chromosomal Mapping with the FISH Method

Seventy four out of 100 mitotic figures showed signal on one pair of the X chromosome. This is shown by FIGS. 12A and 12B. Since DAPI was used to identify the specific chromosomes, the assignment between signal from the cDNA probe and the long arm of chromosome X was obtained. The detailed position of nmt55 gene was further assessed from the summary analyses of 10 photographs, and was assigned to the long arm of chromosome X q13, as depicted in FIG. 13. Additional loci for nmt 5 were not detected using the FISH method.

Conclusions Drawn from Experiments and Empirical Data

1. The empirical data has identified and characterized a 55 kDa protein (nmt55) using a site-directed monoclonal antibodies to a unique peptide derived from human ER. Although NMT-1 monoclonal antibody was raised against a peptide from ER, NMT-1 failed to react with denatured ER in Westernblot analyses. This observation shows that the epitope for this antibody on ER is very sensitive to conformational changes; and once denatured by SDS, it could not be recognized in ER. In contrast, this epitope appears to be stable or capable of renaturation in nmt55, as demonstrated by consistent detection by Westernblot analyses.

2. The nmt55 protein did not bind estradiol, and did not cross-react with antibodies specific to ER. These observations revealed that nmt55 was not an ER variant; it also did not associated with ER, as assessed by sucrose density gradient analysis and subsequent Western blotting. nmt55 protein was localized mainly to the nucleus and is found in many tissues of animal species. This shows that nmt55 is conserved and has an important role in cellular regulation.

3. nmt55 expression was detected in normal breast tissue biopsies, and in most ER+/PR+ breast tumors, but not expressed in all of ER– human breast tumors. Loss of ER expression in human breast tumors is often associated with poor prognosis, while continued expression of ER is associated with disease-free survival and correlates well with tumor state of differentiation. It is believed that the loss of nmt55 expression in the majority of ER– human breast tumors is thus directly related to loss of regulation of normal cellular growth and function.

4. Evaluation of tumor pathological characteristics and hormonal status and the relationship with nmt55 expression showed an association with ER status, PR status, tumor hormone phenotype and mean tumor size. The association of tumor size with loss of nmt55 expression demonstrates the role for this protein in tumor growth, invasion or metastases. Since tumor size is clinically used as an indicator of tumor metastases the loss of nmt55 expression in tumors is indicative of tumor progression to metastases; and that loss of nmt55 is a clinical and diagnostic marker for tumor metastases. PR was independent predictor of nmt55 protein expression. Because PR is under estrogen control, the observed relationship between tumor hormonal status and nmt55 expression is related to estrogen receptor function. Tumors which continue to express ER but not PR (ER+/PR–) may also express non-functional ER; such tumors are progressing to a poor state of differentiation.

5. The cloned cDNA for nmt55 from a human breast tumor cell line has a predicted open reading frame which encodes a 471 amino acid protein having a calculated molecular weight of 54,169 Da. The deduced amino acid sequence of this protein indicates that it is a basic protein with an estimated pH of 9.5. Based on homology with other proteins, nmt55 protein has two RNA recognition motifs (RRM), suggesting that it is an RNA binding protein. The presence of a region with helix-turn-helix structure in nmt55 shows that nmt55 binds to DNA.

The present invention is not to be restricted in form nor limited in scope except by the claims appended hereto.

What I claim is:

1. An in-vitro DNA test method for diagnosing whether a primary breast tumor from an individual human subject is a clinically metastatic tumor, said in-vitro DNA test method comprising the steps of:

obtaining a specimen of breast tumor cells representative of a primary tumor found clinically in the breast of an individual human subject;

fractionating said specimen to yield nuclear DNA from the nuclear components of the primary breast tumor cells as a discrete fraction;

separating at least a part of said nuclear DNA fraction from said fractionated primary breast tumor cell specimen; and detecting an absence of DNA specifically coding for the nmt55 protein in said separated DNA fraction, said detected absence of DNA specifically coding for the nmt55 protein in said separated DNA indicating that the primary breast tumor found in the individual human subject is a clinically metastatic tumor.

2. The in-vitro DNA test method as recited in claim 1 wherein said detection comprises a Southern blot assay.

* * * * *

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
        (A) LENGTH: 471 amino acids
        (B) TYPE: amino acid
        (D) TOPOLOGY: linear (xi) SEQUENCE DESCRIPTION: SEQ ID NO: 1:

```
Met Gln Ser Asn Lys Thr Phe Asn Leu Glu Lys Gln Asn His Thr Pro
1               5                   10                  15

Arg Lys His His Gln His His His Gln Gln Gln His His Gln Gln Gln
                20                  25                  30

Gln Gln Gln Pro Pro Pro Pro Ile Pro Ala Asn Gly Gln Gln Ala
            35                  40                  45

Ser Ser Gln Asn Glu Gly Leu Thr Ile Asp Leu Lys Asn Phe Arg Lys
    50                  55                  60
```

```
Pro Gly Glu Lys Thr Phe Thr Gln Arg Ser Arg Leu Phe Val Gly Asn
 65                  70                  75                  80

Leu Pro Pro Asp Ile Thr Glu Glu Met Arg Lys Leu Phe Glu Lys
                 85                  90                  95

Tyr Gly Lys Ala Gly Glu Val Phe Ile His Lys Asp Lys Gly Phe Gly
                100                 105                 110

Phe Ile Arg Leu Glu Thr Arg Thr Leu Ala Glu Ile Ala Lys Val Glu
             115                 120                 125

Leu Asp Asn Met Pro Leu Arg Gly Lys Gln Leu Arg Val Arg Phe Ala
     130                 135                 140

Cys His Ser Ala Ser Leu Thr Val Arg Asn Leu Pro Gln Tyr Val Ser
145                 150                 155                 160

Asn Glu Leu Leu Glu Glu Ala Phe Ser Val Phe Gly Gln Val Glu Arg
                165                 170                 175

Ala Val Val Ile Val Asp Asp Arg Gly Arg Pro Ser Gly Lys Gly Ile
             180                 185                 190

Val Glu Phe Ser Gly Lys Pro Ala Ala Arg Lys Ala Leu Asp Arg Cys
         195                 200                 205

Ser Glu Gly Ser Phe Leu Leu Thr Thr Phe Pro Arg Pro Val Thr Val
    210                 215                 220

Glu Pro Met Asp Gln Leu Asp Asp Glu Glu Gly Leu Pro Glu Lys Leu
225                 230                 235                 240

Val Ile Lys Asn Gln Gln Phe His Lys Glu Arg Glu Gln Pro Pro Arg
                245                 250                 255

Phe Ala Gln Pro Gly Ser Phe Glu Tyr Glu Tyr Ala Met Arg Trp Lys
                260                 265                 270

Ala Leu Ile Glu Met Glu Lys Gln Gln Gln Asp Gln Val Asp Arg Asn
             275                 280                 285

Ile Lys Glu Ala Arg Glu Lys Leu Glu Met Glu Met Glu Ala Ala Arg
     290                 295                 300

His Glu His Gln Val Met Leu Met Arg Gln Asp Leu Met Arg Arg Gln
305                 310                 315                 320

Glu Glu Leu Arg Arg Met Glu Glu Leu His Asn Gln Glu Val Gln Lys
                325                 330                 335

Arg Lys Gln Leu Glu Leu Arg Gln Glu Glu Arg Arg Arg Arg Glu
                340                 345                 350

Glu Glu Met Arg Arg Gln Gln Glu Met Met Arg Arg Gln Gln Glu
    355                 360                 365

Gly Phe Lys Gly Thr Phe Pro Asp Ala Arg Glu Gln Glu Ile Arg Met
    370                 375                 380

Gly Gln Met Ala Met Gly Gly Ala Met Gly Ile Asn Asn Arg Gly Ala
385                 390                 395                 400

Met Pro Pro Ala Pro Val Pro Ala Gly Thr Pro Ala Pro Pro Gly Pro
                405                 410                 415

Ala Thr Met Met Pro Asp Gly Thr Leu Gly Leu Thr Pro Thr Thr
             420                 425                 430

Glu Arg Phe Gly Gln Ala Ala Thr Met Glu Gly Ile Gly Ala Ile Gly
         435                 440                 445

Gly Thr Pro Pro Ala Phe Asn Arg Ala Ala Pro Gly Ala Glu Phe Ala
         450                 455                 460

Pro Asn Lys Arg Arg Tyr
465                 470
```

(2) INFORMATION FOR SEQ ID NO: 2:

(i) SEQUENCE CHARACTERISTICS:
        (A) LENGTH: 1416
        (B) TYPE: nucleic acid
        (C) STRANDEDNESS: single
        (D) TOPOLOGY: linear (xi) SEQUENCE DESCRIPTION: SEQ ID NO: 2:

```
ATG CAG AGT AAT AAA ACT TTT AAC TTG GAG AAG CAA AAC CAT ACT CCA      48
AGA AAG CAT CAT CAA CAT CAC CAC CAG CAG CAG CAC CAC CAG CAG CAA      96
CAG CAG CAG CCG CCA CCA CCG CCA ATA CCT GCA AAT GGG CAA CAG GCC     144
AGC AGC CAA AAT GAA GGC TTG ACT ATT GAC CTG AAG AAT TTT AGA AAA     192
CCA GGA GAG AAG ACC TTC ACC CAA CGA AGC CGT CTT TTT GTG GGA AAT     240
CTT CCT CCC GAC ATC ACT GAG GAA GAA ATG AGG AAA CTA TTT GAG AAA     288
TAT GGA AAG GCA GGC GAA GTC TTC ATT CAT AAG GAT AAA GGA TTT GGC     336
TTT ATC CGC TTG GAA ACC CGA ACC CTA GCG GAG ATT GCC AAA GTG GAG     384
CTG GAC AAT ATG CCA CTC CGT GGA AAG CAG CTG CGT GTG CGC TTT GCC     432
TGC CAT AGT GCA TCC CTT ACA GTT CGA AAC CTT CCT CAG TAT GTG TCC     480
AAC GAA CTG CTG GAA GAA GCC TTT TCT GTG TTT GGC CAG GTA GAG AGG     528
GCT GTA GTC ATT GTG GAT GAT CGA GGA AGG CCC TCA GGA AAA GGC ATT     576
GTT GAG TTC TCA GGG AAG CCA GCT GCT CGG AAA GCT CTG GAC AGA TGC     624
AGT GAA GGC TCC TTC CTG CTA ACC ACA TTT CCT CGT CCT GTG ACT GTG     672
GAG CCC ATG GAC CAG TTA GAT GAT GAA GAG GGA CTT CCA GAG AAG CTG     720
GTT ATA AAA AAC CAG CAA TTT CAC AAG GAA CGA GAG CAG CCA CCC AGA     768
TTT GCA CAG CCT GGC TCC TTT GAG TAT GAA TAT GCC ATG CGC TGG AAG     816
GCA CTC ATT GAG ATG GAG AAG CAG CAG CAG GAC CAA GTG GAC CGC AAC     864
ATC AAG GAG GCT CGT GAG AAG CTG GAG ATG GAG ATG GAA GCT GCA CGC     912
CAT GAG CAC CAG GTC ATG CTA ATG AGA CAG GAT TTG ATG AGG CGC CAA     960
GAA GAA CTT CGG AGG ATG GAA GAG CTG CAC AAC CAA GAG GTG CAA AAA    1008
CGA AAG CAA CTG GAG CTC AGG CAG GAG GAA GAG CGC AGG CGC CGT GAA    1056
GAA GAG ATG CGG CGG CAG CAA GAA GAA ATG ATG CGG CGA CAG CAG GAA    1104
GGA TTC AAG GGA ACC TTC CCT GAT GCG AGA GAG CAG GAG ATT CGG ATG    1152
GGT CAG ATG GCT ATG GGA GGT GCT ATG GGC ATA AAC AAC AGA GGT GCC    1200
ATG CCC CCT GCT CCT GTG CCA GCT GGT ACC CCA GCT CCT CCA GGA CCT    1248
GCC ACT ATG ATG CCG GAT GGA ACT TTG GGA TTG ACC CCA CCA ACA ACT    1296
GAA CGC TTT GGT CAG CTG CTA CA ATG GAA GGA ATT GGG CA ATT GGT      1344
```
```
GGA ACT CCT CCT GCA TTC AAC CGT GCA GCT CCT GGA GCT GAA TTT GCC    1392
CCA AAC AAA CGT CGC CGA TAC TAA                                   1416
```

(2) INFORMATION FOR SEQ ID NO: 3:

(i) SEQUENCE CHARACTERISTICS:
        (A) LENGTH: 15 amino acids
        (B) TYPE: amino acid
        (D) TOPOLOGY: linear -continued (xi) SEQUENCE DESCRIPTION: SEQ ID NO: 3:

```
Thr Val Arg Glu Ala Gly Pro Pro Ala Phe Tyr Arg Pro Asn Ser
1               5                   10                  15
```

(2) INFORMATION FOR SEQ ID NO: 4:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO: 4:

```
Ala Ala Pro Gly Ala
1               5
```

(2) INFORMATION FOR SEQ ID NO: 5:

(i) SEQUENCE CHARACTERISTICS:
        (A) LENGTH: 154 amino acids
        (B) TYPE: amino acid
        (D) TOPOLOGY: linear (xi) SEQUENCE DESCRIPTION: SEQ ID NO: 5:

```
Arg Leu Phe Val Gly Asn Leu Pro Pro Asp Ile Thr Glu Glu Met
1               5                   10                  15

Arg Lys Leu Phe Glu Lys Tyr Gly Lys Ala Gly Glu Val Phe Ile His
                20                  25                  30

Lys Asp Lys Gly Phe Gly Phe Ile Arg Leu Glu Thr Arg Thr Leu Ala
            35                  40                  45

Glu Ile Ala Lys Val Glu Leu Asp Asn Met Pro Leu Arg Gly Lys Gln
        50                  55                  60

Leu Arg Val Arg Phe Ala Cys His Ser Ala Ser Leu Thr Val Arg Asn
65                  70                  75                  80

Leu Pro Gln Tyr Val Ser Asn Glu Leu Leu Glu Glu Ala Phe Ser Val
                85                  90                  95

Phe Gly Gln Val Glu Arg Ala Val Val Ile Val Asp Asp Arg Gly Arg
                100                 105                 110

Pro Ser Gly Lys Gly Ile Val Glu Phe Ser Gly Lys Pro Ala Ala Arg
            115                 120                 125

Lys Ala Leu Asp Arg Cys Ser Glu Gly Ser Phe Leu Leu Thr Thr Phe
        130                 135                 140

Pro Arg Pro Val Thr Val Glu Pro Met Asp
145                 150
```

(2) INFORMATION FOR SEQ ID NO: 6:

(i) SEQUENCE CHARACTERISTICS:
        (A) LENGTH: 154 amino acids
        (B) TYPE: amino acid
        (D) TOPOLOGY: linear (xi) SEQUENCE DESCRIPTION: SEQ ID NO: 6:

```
Arg Leu Phe Val Gly Asn Leu Pro Pro Asp Ile Thr Glu Glu Met
1               5                   10                  15

Arg Lys Leu Phe Glu Lys Tyr Gly Lys Ala Gly Glu Val Phe Ile His
                20                  25                  30

Lys Asp Lys Gly Phe Gly Phe Ile Arg Leu Glu Thr Arg Thr Leu Ala
            35                  40                  45

Glu Ile Ala Lys Val Glu Leu Asp Asn Met Pro Leu Arg Gly Lys Gln
        50                  55                  60
```

```
Leu Arg Val Arg Phe Ala Cys His Ser Ala Ser Leu His Val Arg Asn
 65                  70                  75                  80

Leu Pro Gln Tyr Val Ser Asn Glu Leu Leu Glu Glu Ala Phe Ser Val
                 85                  90                  95

Phe Gly Gln Val Glu Arg Ala Val Val Ile Val Asp Asp Arg Gly Arg
                100                 105                 110

Pro Ser Gly Lys Gly Ile Val Glu Phe Ser Gly Lys Pro Ala Ala Arg
                115                 120                 125

Lys Ala Leu Asp Arg Cys Ser Glu Gly Ser Phe Leu Leu Thr Thr Phe
130                 135                 140

Pro Arg Pro Val Thr Val Glu Pro Met Asp
145                 150

(2) INFORMATION FOR SEQ ID NO: 7:

(i) SEQUENCE CHARACTERISTICS:
        (A) LENGTH: 154 amino acids
        (B) TYPE: amino acid
        (D) TOPOLOGY: linear (xi) SEQUENCE DESCRIPTION: SEQ ID NO: 7:

Arg Leu Phe Val Gly Asn Leu Pro Pro Asp Ile Thr Glu Glu Glu Met
1               5                   10                  15

Arg Lys Leu Phe Glu Lys Tyr Gly Lys Ala Gly Glu Val Phe Ile His
                20                  25                  30

Lys Asp Lys Gly Phe Gly Phe Ile Arg Leu Glu Thr Arg Thr Leu Ala
            35                  40                  45

Glu Ile Val Lys Val Glu Leu Asp Asn Met Pro Leu Arg Gly Lys Gln
 50                  55                  60

Leu Arg Val Arg Phe Ala Cys His Ser Ala Ser Leu Thr Val Arg Asn
 65                  70                  75                  80

Leu Pro Gln Tyr Val Ser Asn Glu Leu Leu Glu Glu Ala Phe Ser Val
                 85                  90                  95

Phe Gly Gln Val Glu Arg Ala Val Val Ile Val Asp Asp Arg Gly Arg
                100                 105                 110

Pro Ser Gly Lys Gly Ile Val Glu Phe Ser Gly Lys Pro Ala Ala Arg
                115                 120                 125

Lys Ala Leu Asp Arg Cys Ser Glu Gly Ser Phe Leu Leu Thr Thr Phe
130                 135                 140

Pro Arg Pro Val Thr Val Glu Pro Met Asp
145                 150

(2) INFORMATION FOR SEQ ID NO: 8:

(i) SEQUENCE CHARACTERISTICS:
        (A) LENGTH: 154 amino acids
        (B) TYPE: amino acid
        (D) TOPOLOGY: linear (xi) SEQUENCE DESCRIPTION: SEQ ID NO: 8:

Arg Leu Phe Val Gly Asn Leu Pro Ala Asp Ile Thr Glu Asp Glu Phe
1               5                   10                  15

Lys Arg Leu Phe Ala Lys Tyr Gly Glu Pro Gly Glu Val Phe Ile Asn
                20                  25                  30

Lys Gly Lys Gly Phe Gly Phe Ile Lys Leu Glu Ser Arg Ala Leu Ala
            35                  40                  45

Glu Ile Ala Lys Ala Glu Leu Asp Asp Thr Pro Met Arg Gly Arg Gln
```

```
            50                  55                  60
Leu Arg Val Arg Phe Ala Thr His Ala Ala Ala Leu Ser Val Arg Asn
 65                  70                  75                  80

Leu Ser Pro Tyr Val Ser Asn Glu Leu Leu Glu Glu Ala Phe Ser Gln
                 85                  90                  95

Phe Gly Pro Ile Glu Arg Ala Val Val Ile Val Asp Asp Arg Gly Arg
                100                 105                 110

Ser Thr Gly Lys Gly Ile Val Glu Phe Ala Ser Lys Pro Ala Ala Arg
                115                 120                 125

Lys Ala Phe Glu Arg Cys Ser Glu Gly Val Phe Leu Leu Thr Thr Thr
130                 135                 140

Pro Arg Pro Val Ile Val Glu Pro Leu Glu
145                 150
```

(2) INFORMATION FOR SEQ ID NO: 9:

(i) SEQUENCE CHARACTERISTICS:
        (A) LENGTH: 154 amino acids
        (B) TYPE: amino acid
        (D) TOPOLOGY: linear (xi) SEQUENCE DESCRIPTION: SEQ ID NO: 9:

```
Arg Leu Tyr Val Gly Asn Leu Thr Asn Asp Ile Thr Asp Asp Glu Leu
  1                  5                  10                  15

Arg Glu Met Phe Lys Pro Tyr Gly Glu Ile Ser Glu Ile Phe Ser Asn
                 20                  25                  30

Leu Asp Lys Asn Phe Thr Phe Leu Lys Val Asp Tyr His Pro Asn Ala
                 35                  40                  45

Glu Lys Ala Lys Arg Ala Leu Asp Gly Ser Met Arg Lys Gly Arg Gln
 50                  55                  60

Leu Arg Val Arg Phe Ala Pro Asn Ala Thr Ile Leu Arg Val Ser Asn
 65                  70                  75                  80

Leu Thr Pro Phe Val Ser Asn Glu Leu Leu Tyr Lys Ser Phe Glu Ile
                 85                  90                  95

Phe Gly Pro Ile Glu Arg Ala Ser Ile Thr Val Asp Asp Arg Gly Lys
                100                 105                 110

His Met Gly Glu Gly Ile Val Glu Phe Ala Lys Lys Ser Ser Ala Ser
                115                 120                 125

Ala Cys Leu Arg Met Cys Asn Glu Lys Cys Phe Phe Leu Thr Ala Ser
130                 135                 140

Leu Arg Pro Cys Leu Val Glu Pro Met Glu
145                 150
```

(2) INFORMATION FOR SEQ ID NO: 10:

(i) SEQUENCE CHARACTERISTICS:
        (A) LENGTH: 49 amino acids
        (B) TYPE: amino acid
        (D) TOPOLOGY: linear (xi) SEQUENCE DESCRIPTION: SEQ ID NO: 10:

```
Arg Asn Ile Lys Glu Ala Arg Glu Lys Leu Glu Met Glu Met Glu Ala
  1                  5                  10                  15

Ala Arg His Glu His Gln Val Met Leu Met Gln Gln Asp Leu Met Arg
                 20                  25                  30

Arg Gln Glu Glu Leu Arg Arg Met Glu Glu Leu His Asn Gln Glu Val
                 35                  40                  45
```

-continued

```
Gln (2) INFORMATION FOR SEQ ID NO: 11:

(i) SEQUENCE CHARACTERISTICS:
        (A) LENGTH: 49 amino acids
        (B) TYPE: amino acid
        (D) TOPOLOGY: linear (xi) SEQUENCE DESCRIPTION: SEQ ID NO: 11:

Arg Asn Ile Lys Glu Ala Arg Glu Lys Leu Glu Met Glu Met Glu Ala
1               5                   10                  15

Ala Arg His Glu His Gln Val Met Leu Met Gln Gln Asp Leu Met Arg
            20                  25                  30

Arg Gln Glu Glu Leu Arg Arg Met Glu Glu Leu His Asn Gln Glu Val
        35                  40                  45

Gln (2) INFORMATION FOR SEQ ID NO: 12:

(i) SEQUENCE CHARACTERISTICS:
        (A) LENGTH: 49 amino acids
        (B) TYPE: amino acid
        (D) TOPOLOGY: linear (xi) SEQUENCE DESCRIPTION: SEQ ID NO: 12:

Arg Asn Ile Lys Glu Ala Arg Glu Lys Leu Glu Met Glu Met Glu Ala
1               5                   10                  15

Ala Arg His Glu His Gln Val Met Leu Met Gln Gln Asp Leu Met Arg
            20                  25                  30

Arg Gln Glu Glu Leu Arg Arg Met Glu Glu Leu His Asn Gln Glu Val
        35                  40                  45

Gln
```